United States Patent [19]

Wareing

[11] Patent Number: 4,668,794

[45] Date of Patent: May 26, 1987

[54] INTERMEDIATE IMIDAZOLE ACROLEIN ANALOGS

[75] Inventor: James R. Wareing, Randolph, N.J.

[73] Assignee: Sandoz Pharm. Corp., E. Hanover, N.J.

[21] Appl. No.: 736,679

[22] Filed: May 22, 1985

[51] Int. Cl.[4] ............................................ C07D 233/64
[52] U.S. Cl. .................................... 548/342; 548/110; 548/343
[58] Field of Search ........................................ 548/342

[56] References Cited

U.S. PATENT DOCUMENTS

| | | | |
|---|---|---|---|
| 3,983,140 | 9/1976 | Endo et al. ........................... | 549/292 |
| 4,198,425 | 4/1980 | Mitsui et al. ........................ | 514/460 |
| 4,248,889 | 2/1981 | Oka et al. ............................. | 514/532 |
| 4,255,444 | 3/1981 | Oka et al. ............................. | 514/460 |
| 4,308,378 | 12/1981 | Stokker ................................. | 549/292 |
| 4,351,844 | 9/1982 | Patchett et al. ..................... | 514/460 |
| 4,361,515 | 11/1982 | Terahara et al. .................... | 549/292 |
| 4,375,475 | 3/1983 | Willard et al. ....................... | 514/460 |
| 4,376,863 | 3/1983 | Lam ...................................... | 549/292 |
| 4,387,242 | 6/1983 | Lam ...................................... | 560/119 |
| 4,440,927 | 4/1984 | Prugh .................................... | 549/292 |
| 4,474,971 | 10/1984 | Wareing ................................ | 549/214 |
| 4,503,072 | 3/1985 | Hoffman et al. ..................... | 514/529 |
| 4,530,922 | 7/1985 | Moberg ................................. | 548/110 X |

FOREIGN PATENT DOCUMENTS

| | | | |
|---|---|---|---|
| 895445 | 4/1983 | Belgium .............................. | 549/292 |
| 38061 | 10/1981 | European Pat. Off. ............. | 568/437 |
| 68038 | 1/1983 | European Pat. Off. ............. | 549/292 |
| 56-7775 | 1/1981 | Japan ................................... | 549/292 |
| WO84/02131 | 6/1984 | PCT Int'l Appl. .................. | 549/292 |
| WO84/02903 | 8/1984 | PCT Int'l Appl. .................. | 548/466 |

OTHER PUBLICATIONS

F. Hulcher, *Arch. Biochem. Biophys.*, 146, 422–427 (1971).
A. Sato, et al., *Chem. Pharm. Bull.*, 28, 1509–1525 (1980).
F. Singer, et al., *Proc. Soc. Exp. Biol. Med.*, 102, 370–373 (1959).

*Primary Examiner*—Richard A. Schwartz
*Attorney, Agent, or Firm*—Gerald D. Sharkin; Richard E. Vila; Melvyn M. Kassenoff

[57] ABSTRACT

Compounds of the formula

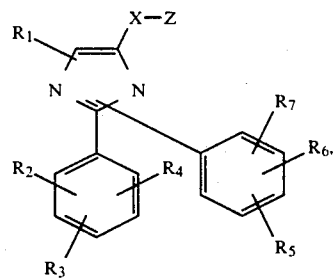

and the pharmaceutically acceptable acid addition salts thereof, wherein the various substituents are defined hereinbelow, the use thereof for inhibiting cholesterol biosynthesis and lowering the blood cholesterol level and, therefore, in the treatment of hyperlipoproteinemia and atherosclerosis, pharmaceutical compositions comprising such compounds and processes for and intermediates in the synthesis of such compounds.

11 Claims, No Drawings

INTERMEDIATE IMIDAZOLE ACROLEIN ANALOGS

This invention relates to compounds of the formula

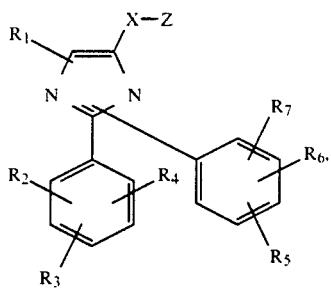

and the pharmaceutically acceptable acid addition salts thereof, wherein $R_1$ is $C_{1-6}$alkyl not containing an asymmetric carbon atom, each of $R_2$ and $R_5$ is independently hydrogen, $C_{1-3}$alkyl, n-butyl, i-butyl, t-butyl, $C_{1-3}$alkoxy, n-butoxy, i-butoxy, trifluoromethyl, fluoro, chloro, phenyl, phenoxy or benzyloxy, each of $R_3$ and $R_6$ is independently hydrogen, $C_{1-3}$alkyl, $C_{1-3}$alkoxy, trifluoromethyl, fluoro, chloro, phenoxy or benzyloxy, each of $R_4$ and $R_7$ is independently hydrogen, $C_{1-2}$alkyl, $C_{1-2}$alkoxy, fluoro or chloro, with the provisos that not more than one of $R_2$ and $R_3$ is trifluoromethyl, not more than one of $R_2$ and $R_3$ is phenoxy, not more than one of $R_2$ and $R_3$ is benzyloxy, not more than one of $R_5$ and $R_6$ is trifluoromethyl, not more than one of $R_5$ and $R_6$ is phenoxy, and not more than one of $R_5$ and $R_6$ is benzyloxy, X is $-CH_2CH_2-$ or $-CH=CH-$,
and Z is $$\text{(a)} \quad -\overset{5}{C}H-CH_2-\overset{3}{C}H-CH_2-COOR_{11} \quad \text{or}$$
$$\phantom{xxxx}\underset{OH}{|}\phantom{xxx}\underset{OH}{|}$$

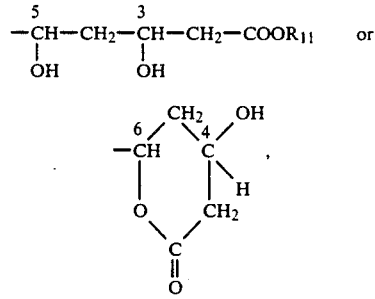

wherein
$R_{11}$ is hydrogen, $R_{12}$ or M,
wherein
$R_{12}$ is a physiologically acceptable and hydrolyzable ester group, and
M is a pharmaceutically acceptable cation,
with the proviso that the compounds must be in free base form when Z contains an M,
processes for and intermediates in the synthetsis thereof, pharmaceutical compositions comprising a compound of Formula I or a pharmaceutically acceptable acid addition salt thereof and the use of the compounds of Formula I and the pharmaceutically acceptable acid addition salts thereof for inhibiting cholesterol biosynthesis and lowering the blood cholesterol level and, therefore, in the treatment of hyperlipoproteinemia and atherosclerosis.

By the term "physiologically acceptable and hydrolyzable ester group" is meant a group which, together with the —COO' radical to which it is attached, forms an ester group which is physiologically acceptable and hydrolyzable under physiological conditions to yield a compound of Formula I wherein $R_{11}$ is hydrogen and an alcohol which itself is physiologically acceptable, i.e., non-toxic at the desired dosage level, and which, preferably, is free of centers of asymmetry. Examples of such groups are $C_{1-3}$alkyl, n-butyl, i-butyl, t-butyl and benzyl, collectively referred to as $R_{12}'$.

The compounds of Formula I except those wherein Z contains an M may be converted into pharmaceutically acceptable acid addition salt form. By the term "pharmaceutically acceptable acid addition salts" is meant those acid addition salts that are physiologically acceptable, i.e., that do not significantly increase the toxicity of the basic compound or otherwise adversely affect its pharmacological activity. Such pharmaceutically acceptable acid addition salts are included within the scope of this invention. Included are salts with strong organic acids, e.g., methanesulfonate, ethanesulfonate, benzenesulfonate and p-toluenesulfonate salts, and salts with strong inorganic acids, e.g., hydrochloride, hydrobromide and sulfate salts. The preferred strong acids are those having a pK (the pK of at least the initial dissociation step if the acid has more than one) in water at 25° C. below about 3, more preferably below about 2 and most preferably below about 1.

The compounds of Formula I and the pharmaceutically acceptable acid addition salts thereof may be divided into two groups, those of Formula IA and those of Formula IB, and the pharmaceutically acceptable acid addition salts thereof.

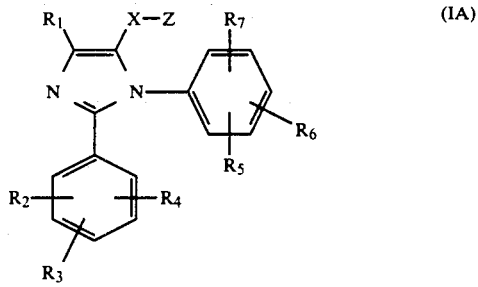

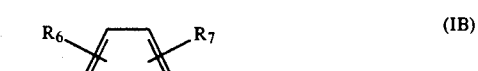

The compounds and pharmaceutically acceptable acid addition salts of each of Groups IA and IB may be divided into two subgroups based upon the significance of Z, viz., Group IAa (those of Group IA wherein Z is a group of Formula a), Group IAb (those of Group IA wherein Z is a group of Formula b), Group IBa (those of Group IB wherein Z is a group of Formula a) and Group IBb (those of Group IB wherein Z is a group of Formula b).

As is self-evident to those in the art, each compound of Formula I (and every subscope and species thereof) has two centers of asymmetry (the two carbon atoms bearing the hydroxy groups in the group of Formula a and the carbon atom bearing the hydroxy group and the carbon atom having the free valence in the group of Formula b) and, therefore, there are four stereoisomeric forms (enantiomers) of each compound (two racemates or pairs of diastereoisomers), provided that $R_{11}$ does not contain any center of asymmetry. The four stereoisomers may be designated as the R,R, R,S, S,R and S,S enantiomers, all four stereoisomers being within the scope of this invention. When $R_{11}$ contains one or more centers of asymmetry, there are eight or more stereoisomers. Since it is preferred that $R_{11}$ not contain a center of asymmetry and for reasons of simplicity any additional stereoisomers resulting from the presence of one or more centers of asymmetry in $R_{11}$ will usually be ignored, it being assumed that $R_{11}$ is free of centers of asymmetry. Each pharmaceutically acceptable acid addition salt contains the same number of centers of asymmetry as the corresponding free base provided that the acid does not contain any center of asymmetry.

$R_1$ is preferably $R_1'$, where $R_1'$ is $C_{1-3}$alkyl, n-butyl or i-butyl, more preferably $R_1''$, where $R_1''$ is $C_{1-3}$alkyl, and most preferably isopropyl.

$R_2$ is preferably $R_2'$, where $R_2'$ is hydrogen, $C_{1-3}$alkyl, $C_{1-2}$alkoxy, trifluoromethyl, fluoro or chloro, more preferably $R_2''$, where $R_2''$ is hydrogen, methyl or fluoro, and most preferably hydrogen.

$R_3$ is preferably $R_3'$, where $R_3'$ is hydrogen, $C_{1-2}$alkyl, fluoro or chloro, more preferably $R_3''$, where $R_3''$ is hydrogen or methyl, and most preferably hydrogen.

$R_4$ is preferably $R_4'$, where $R_4'$ is hydrogen or methyl, and most preferably hydrogen.

Preferably, not more than one of $R_2$ and $R_3$ is a member of the group consisting of t-butyl, trifluoromethyl, phenyl, phenoxy and benzyloxy. More preferably, when any two or all three of $R_2$ ($R_2'$, etc.), $R_3$ ($R_3'$, etc.) and $R_4$ ($R_4'$, etc.) are ortho to each other, at least one member of each pair that are ortho to each other is a member of the group consisting of hydrogen, methyl, methoxy, fluoro and chloro.

The $R_2$-bearing phenyl group is preferably unsubstituted.

$R_5$ is preferably $R_5'$, where $R_5'$ is hydrogen, $C_{1-3}$alkyl, $C_{1-2}$alkoxy, trifluoromethyl, fluoro or chloro, more preferably $R_5''$, where $R_5''$ is hydrogen, methyl or fluoro and most preferably fluoro.

$R_6$ is preferably $R_6'$, where $R_6'$ is hydrogen, $C_{1-2}$alkyl, fluoro or chloro, more preferably $R_6''$, where $R_6''$ is hydrogen or methyl, and most preferably hydrogen.

$R_7$ is preferably $R_7'$, where $R_7'$ is hydrogen or methyl, and most preferably hydrogen.

Preferably, not more than one of $R_5$ and $R_6$ is a member of the group consisting of t-butyl, trifluoromethyl, phenyl, phenoxy and benzyloxy. More preferably, when any two or all three of $R_5$ ($R_5'$, etc.), $R_6$ ($R_6'$, etc.) and $R_7$ ($R_7'$, etc.) are ortho to each other, at least one member of each pair that are ortho to each other is a member of the group consisting of hydrogen, methyl, methoxy, fluoro and chloro.

The $R_5$-bearing phenyl group is preferably 4-fluorophenyl or 3,5-dimethylphenyl, more preferably the former.

$R_{11}$ is preferably $R_{11}'$, where $R_{11}'$ is hydrogen, $R_{12}'$ or M, more preferably $R_{11}''$, where $R_{11}''$ is hydrogen, $C_{1-3}$alkyl or M, even more preferably $R_{11}'''$, where $R_{11}'''$ is hydrogen, $C_{1-2}$alkyl or M and most preferably M, especially sodium.

$R_{12}$ is preferably $R_{12}'$, where $R_{12}'$ is $C_{1-3}$alkyl, n-butyl, i-butyl, t-butyl or benzyl, more preferably $C_{1-3}$alkyl, and most preferably $C_{1-2}$alkyl, especially ethyl.

X is preferably —CH=CH— and most preferably

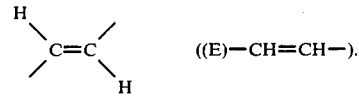

$((E)-CH=CH-)$.

Z is preferably a group of Formula a wherein $R_{11}$ is $R_{11}'$ or a group of Formula b, more preferably a group of Formula a wherein $R_{11}$ is $R_{11}''$ or a group of Formula b, even more preferably a group of Formula a wherein $R_{11}$ or $R_{11}'''$ or a group of Formula b, and most preferably a group of Formula a wherein $R_{11}$ is M, preferably M' and especially sodium. M is preferably free from centers of asymmetry and is more preferably M', i.e., sodium, potassium or ammonium, and most preferably sodium. For simplicity, each formula in which M appears has been written as if M were monovalent and, preferably, it is. However, it may also be divalent or trivalent and, when it is, it balances the charge of two or three carboxy groups, respectively. Thus, Formula I and every other formula containing an M embraces compounds wherein M is divalent or trivalent, i.e., which contains two or three carboxylate-containing anions per cation M.

As between otherwise identical compounds of Formula I and pharmaceutically acceptable acid addition salts thereof, those wherein Z is a group of Formula a are generally preferred over those wherein Z is a group of Formula b.

Insofar as the compounds of Groups IAa and IBa and the pharmaceutically acceptable acid addition salts thereof and each of the subgroups thereof are concerned, the erythro isomers are preferred over the threo isomers, erythro and threo referring to the relative positions of the hydroxy groups in the 3- and 5-positions of the group of Formula a.

Insofar as the compounds of Groups IAb and IBb and the pharmaceutically acceptable acid adition salts thereof and each of the subgroups thereof are concerned, the trans lactones are generally preferred over the cis lactones, cis and trans referring to the relative positions of the hydrogen atoms in the 4- and 6-positions of the group of Formula b.

The preferred stereoisomers of the compounds of Formula I and the pharmaceutically acceptable acid addition salts thereof having only two centers of asymmetry wherein X is —CH=CH—, and Z is a group of Formula a are the 3R,5S isomer and the racemate of which it is a constituent, i.e., the 3R,5S-3S,5R (erythro) racemate.

The preferred stereoisomers of the compounds of Formula I and the pharmaceutically acceptable acid addition salts thereof having only two centers of asymmetry wherein X is —CH$_2$CH$_2$—, and Z is a group of Formula a are the 3R,5R isomer and the racemate of which it is a constitutent, i.e., the 3R,5R-3S,5S (erythro) racemate.

The preferences set forth in the preceding two paragraphs also apply to the compounds of Formula I and the pharmaceutically acceptable acid addition salts thereof having more than two centers of asymmetry and represent the preferred configurations of the indicated positions.

The preferred stereoisomers of the compounds of Formula I and the pharmaceutically acceptable acid addition salts thereof wherein X is —CH=CH—, and Z is a group of Formula b are the 4R,6S and 4R,6R isomers and the racemate of which each is a constituent, i.e., the 4R,6S-4S,6R (trans lacetone) and 4R,6R-4S,6S (cis lactone) racemates, with the 4R,6S isomer and the racemate of which it is a constituent being more preferred and the 4R,6S isomer being most preferred.

The preferred stereoisomers of the compounds of Formula I and the pharmaceutically acceptable acid addition salts thereof wherein X is —CH$_2$CH$_2$—, and Z is a group of Formula b are the 4R,6R and 4R,6S isomers and the racemate of which each is a constituent, i.e., the 4R,6R-4S,6S (trans lacetone) and 4R,6S-4S,6R (cis lacetone) racemates, with the 4R,6R isomer and the racemate of which it is a constituent being more preferred and the 4R,6R isomer being most preferred.

Generally, the compounds of Formula I are preferred over the pharmaceutically acceptable acid addition salts of the corresponding compounds.

Each of the preferences set forth above applies, not only to the compounds of Formula I, but also to the compounds of Formulae IA and IB and the pharmaceutically acceptable acid addition salts thereof and those of Groups IAa, IAb, IBa and IBb as well as to every other subgroup thereof set forth in the specification, e.g., Groups (i) et seq., unless otherwise indicated. When any preference or group contains a variable, the preferred significances of that variable apply to the preference in question, unless otherwise indicated.

Preferred subgroups of Formulae IAa and IAb include the compounds and the pharmaceutically acceptable acid addition salts (i) of Group IAa wherein $R_1$ is $R_1'$, $R_2$ is $R_2'$, $R_3$ is $R_3'$, $R_4$ is $R_4'$, $R_5$ is $R_5'$, $R_6$ is $R_6'$, $R_7$ is $R_7'$, $R_{11}$ is $R_{11}''$, and X is —CH=CH—, (ii) of (i) wherein $R_2$ is $R_2''$, $R_3$ is $R_3''$, $R_4$ is hydrogen, $R_5$ is $R_5''$, $R_6$ is $R_6''$, $R_7$ is hydrogen, $R_{11}$ is $R_{11}'''$, and X is (E)—CH=CH—, (iii) or (ii) wherein $R_1$ is $R_1''$, (iv)-(vi) of (i)-(iii) wherein $R_{11}$ is M, especially sodium, (vii)-(xii) of (i)-(vi) wherein the hydroxy groups in the 3- and 5-positions of the group Formula a have the erythro configuration, (xiii)-(xviii) the 3R,5S enantiomers of the compounds of (vii)-(xii), (xix) of Group IAb wherein $R_1$ is $R_1'$, $R_2$ is $R_2'$, $R_3$ is $R_3'$, $R_4$ is $R_4'$, $R_5$ is $R_5'$, $R_6$ is $R_6'$, $R_7$ is $R_7'$, and X is —CH=CH—, (xx) of (xix) wherein $R_2$ is $R_2''$, $R_3$ is $R_3''$, $R_4$ is hydrogen, $R_5$ is $R_5''$, $R_6$ is $R_6''$, $R_7$ is hydrogen, and X is (E)—CH=CH—, (xxi) of (xx) wherein $R_1$ is $R_1''$, (xxii)-(xxiv) of (xix)-(xxi) wherein the hydrogen atoms in the 4- and 6-positions of the groups of Formula b are trans to each other (i.e., the trans lactones), and (xxv)-(xxvii) the 4R,6S enantiomers of the compounds of (xxii)-(xxiv).

Groups (vii)-(xii) embrace the 3R,5S-3S,5R racemate and the 3R,5S and 3S,5R enantiomers, the 3S,5R enantiomer being least preferred.

Groups (xxii)-(xxiv) embrace the 4R,6S-4S,6R racemate and the 4R,6S and 4S,6R enantiomers, the 4S,6R enantiomer being least preferred.

Insofar as Groups IBa and IBb are concerned, the preferred subgroups are those that correspond to Groups (i)-(xxvii), i.e., Groups (xxviii)-(liv). As should be self-evident, the preferred subgroups of Group IBa are those that correspond to Groups (i)-(xviii), and the preferred subgroups of Group IBb are those that correspond to Groups (xix)-(xxvii).

The free bases of each group that embraces both free bases and pharmaceutically acceptable acid addition salts are preferred.

The compounds of Formula I and the pharmaceutically acceptable acid addition salts thereof may be synthesized as follows:

REACTION SCHEME I

The compounds of Formula I wherein X is —CH=CH—, and Z is a group of Formula b having the 4R,6S configuration or X is —CH$_2$CH$_2$—, and Z is a group of Formula b having the 4R,6R configuration may be synthesized by the following series of reactions:

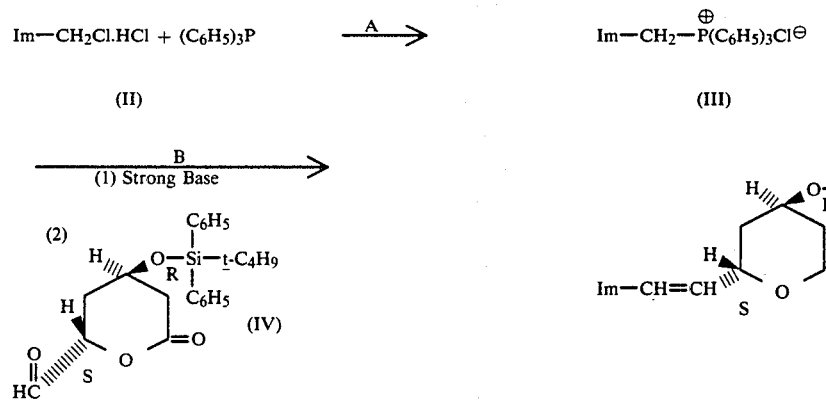

-continued
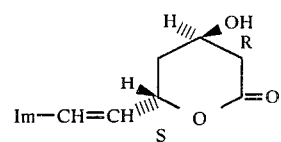
(VI)
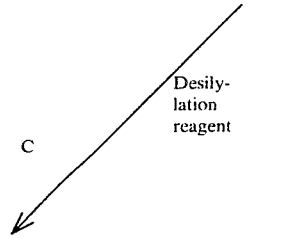
(VII)
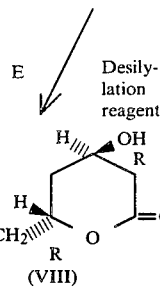
(VIII)
REACTION SCHEME II
The compounds of Formula I wherein Z is a group of Formula a wherein $R_{11}$ is $R_{12}'$ may be synthesized by the following series of reactions:
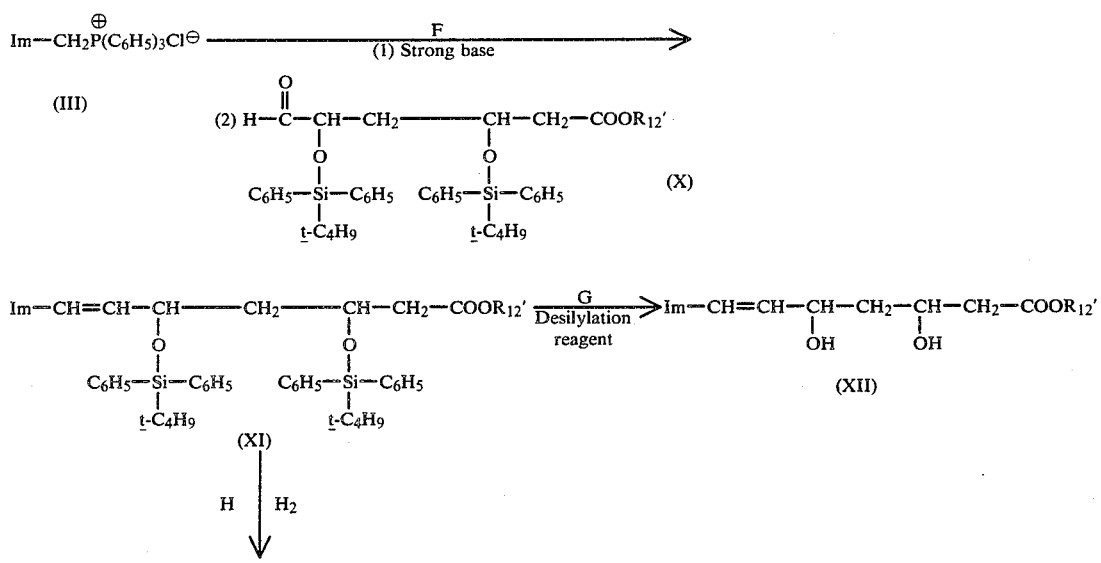

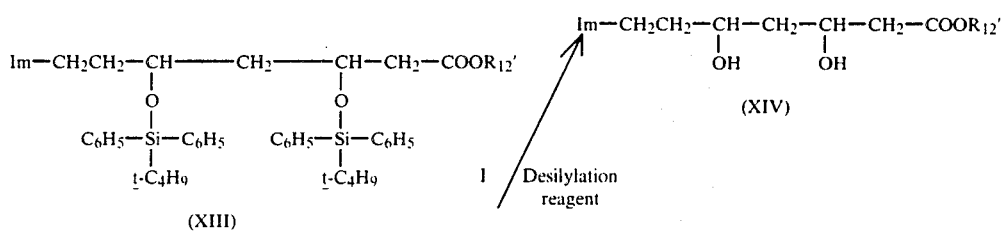

REACTION SCHEME III

The compounds of Formula I wherein X is (E)—CH=CH— or —CH₂CH₂—, and Z is a group of Formula a wherein $R_{11}$ is $R_{12}'$ may also be synthesized by the following series of reactions:

REACTION SCHEME IV

The compounds of Formula I wherein Z is a group of Formula a wherein $R_{11}$ is $R_{12}'$ or a group of Formula b may be converted into the corresponding compounds of Formula I wherein Z has a different significance and the

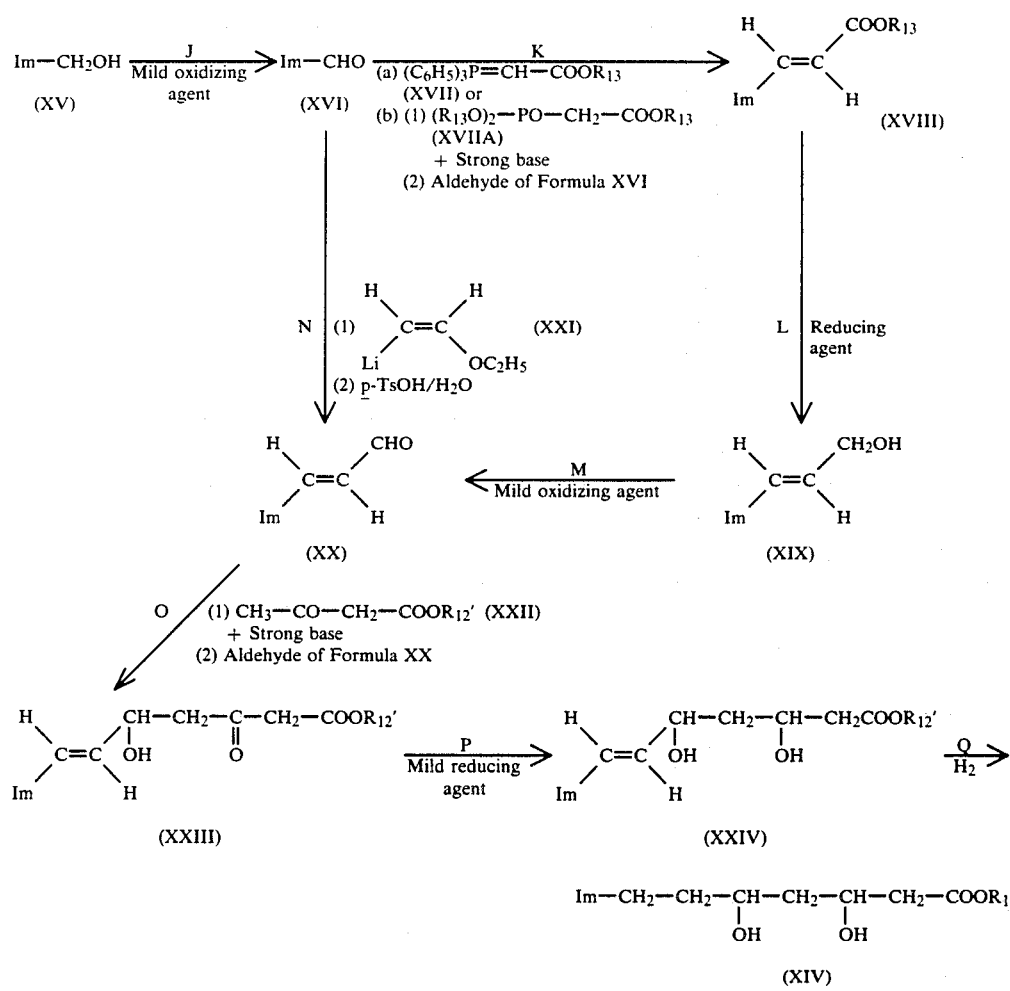

compounds of Formula I except those wherein Z contains an M may be converted into the corresponding pharmaceutically acceptable acid addition salts by the following series of reactions:

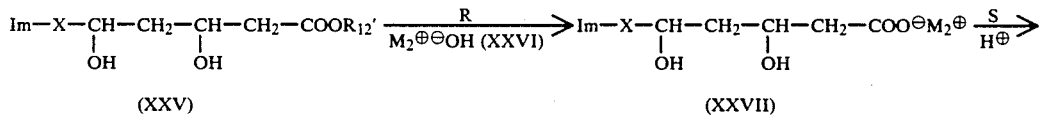

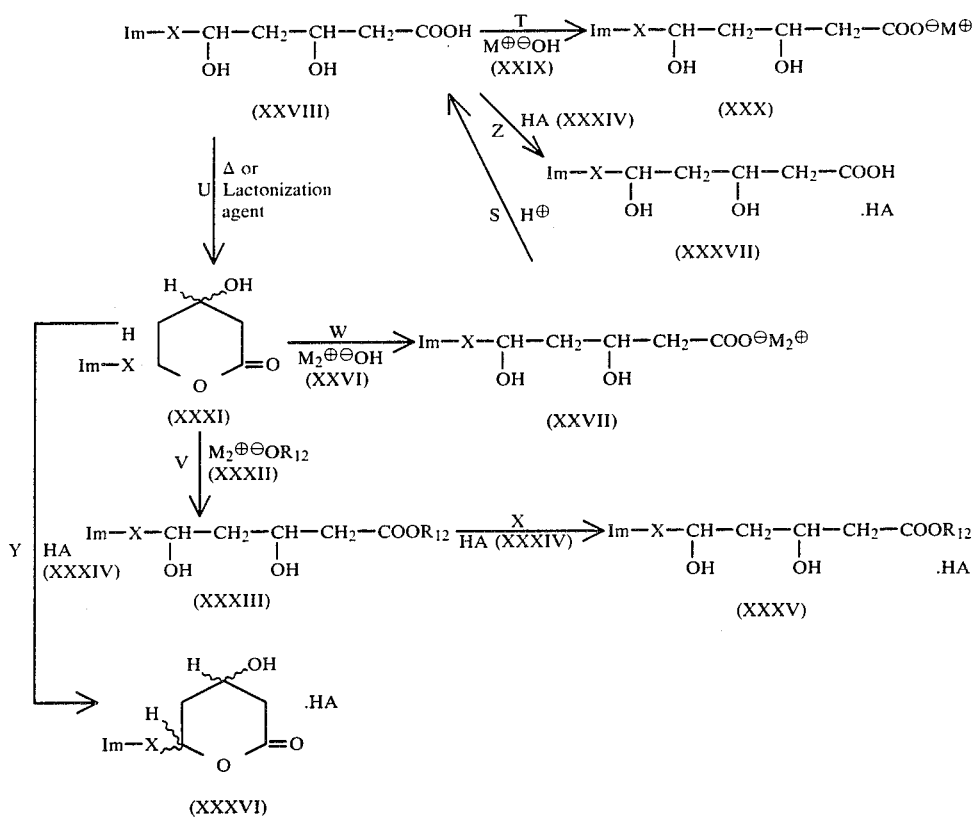
REACTION SCHEME V
The compounds of Formulae II and XV wherein Im is ImA may be synthesized by the following series of reactions:
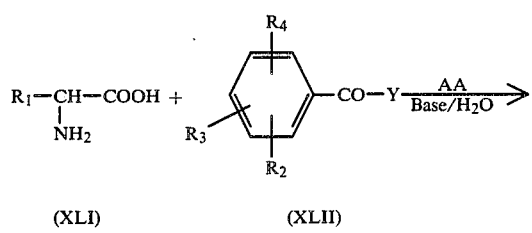
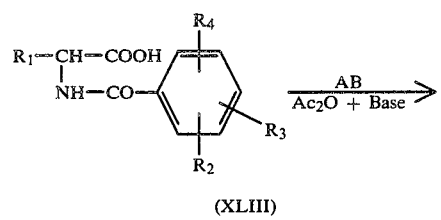
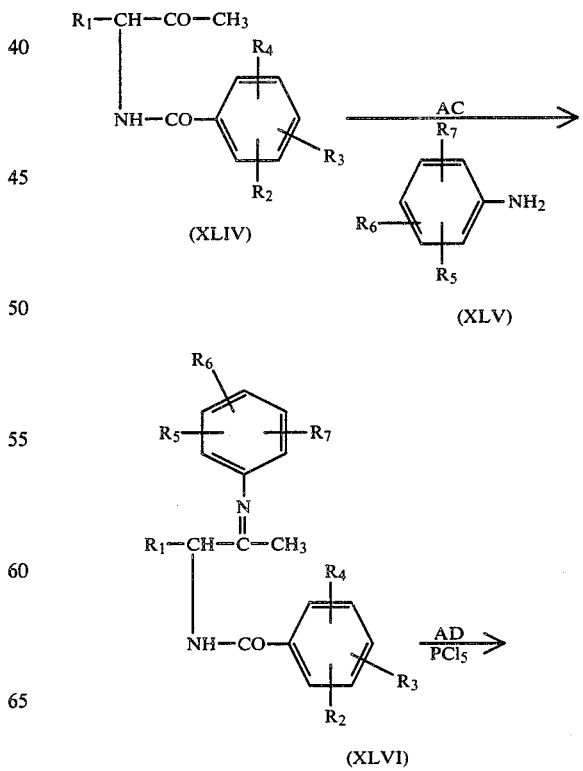

-continued
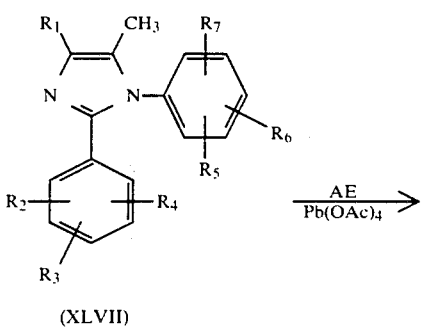
(XLVII)
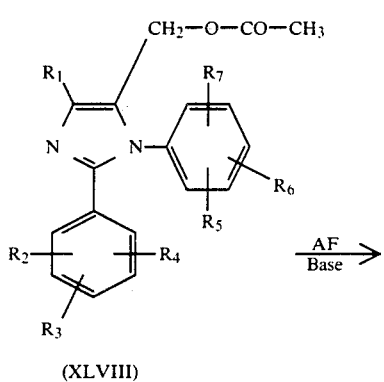
(XLVIII)
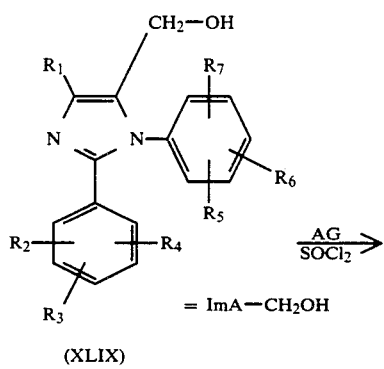
= ImA—CH₂OH
(XLIX)
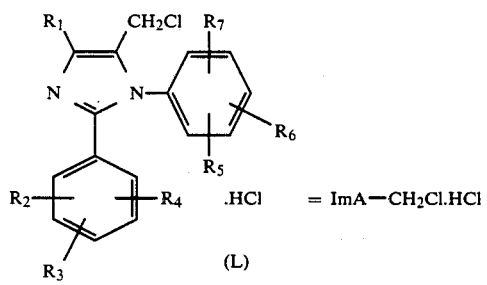
.HCl   = ImA—CH₂Cl.HCl
(L)
REACTION SCHEME VI
The compounds of Formulae II and XV wherein Im is ImB may be synthesized by the following series of reactions:
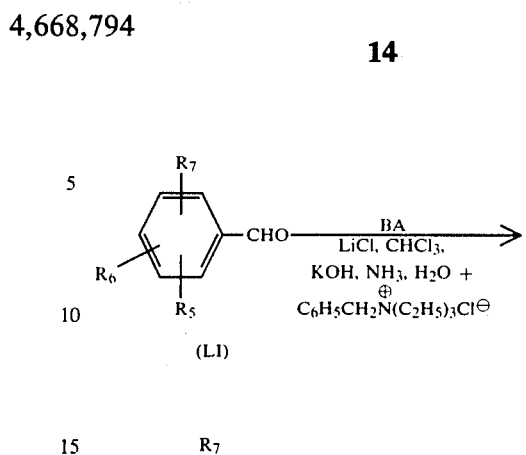
(LI)
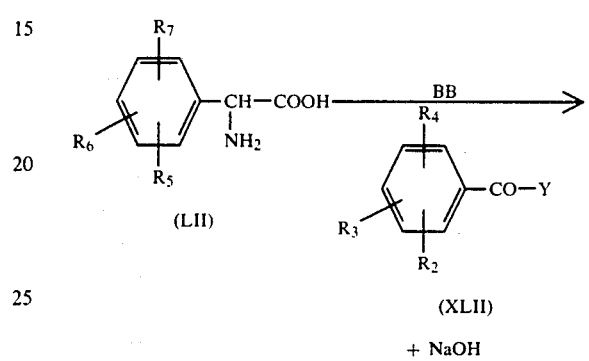
(LII)    (XLII)
+ NaOH
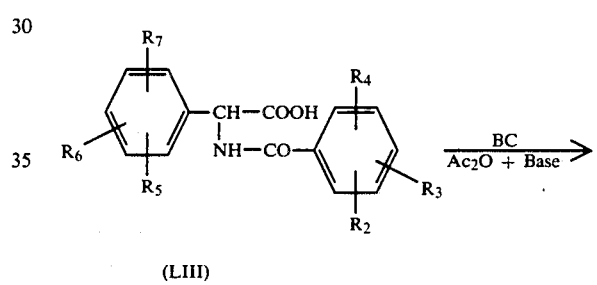
(LIII)
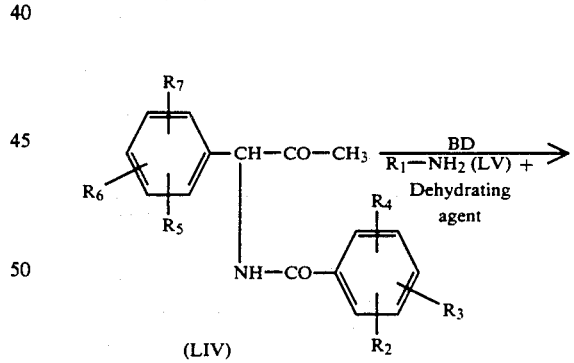
(LIV)
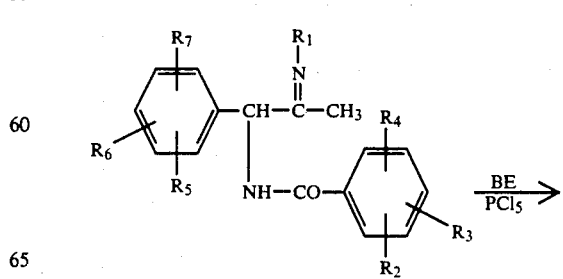
(LVI)

-continued
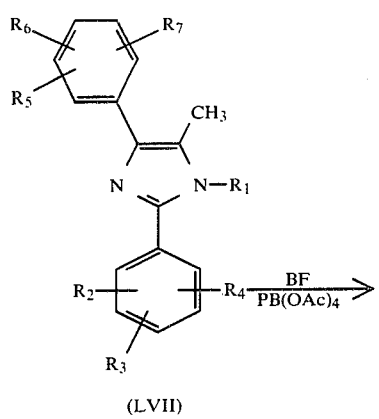
(LVII)
-continued
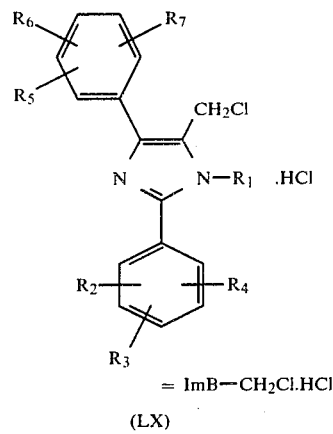
= ImB—CH$_2$Cl.HCl
(LX)
REACTION SCHEME VII
The compound of Formula IV may be synthesized by the following series of reactions:
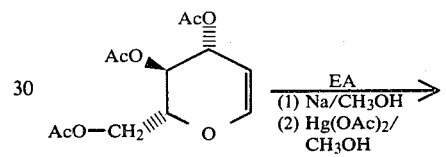
(LXXXI)
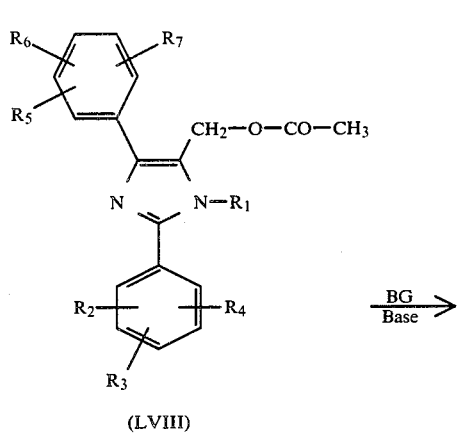
(LVIII)
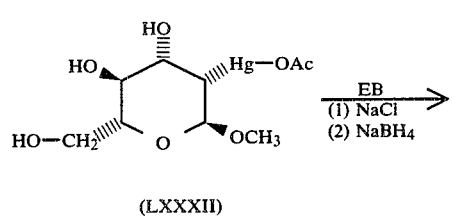
(LXXXII)
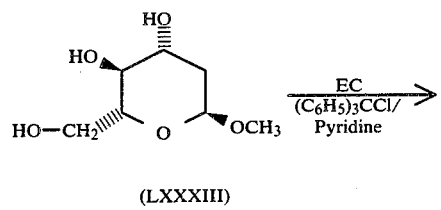
(LXXXIII)
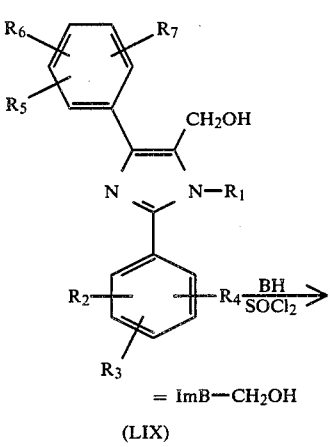
= ImB—CH$_2$OH
(LIX)
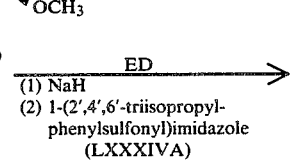
(LXXXIV)
ED
(1) NaH
(2) 1-(2',4',6'-triisopropyl-phenylsulfonyl)imidazole
(LXXXIVA)

-continued
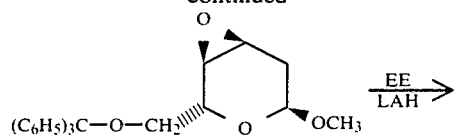
(LXXXV)
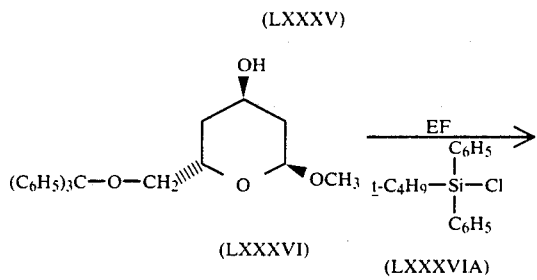
(LXXXVI) (LXXXVIA)
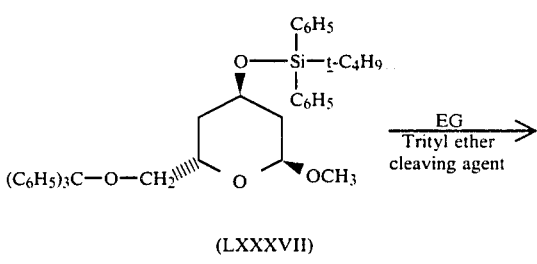
(LXXXVII)
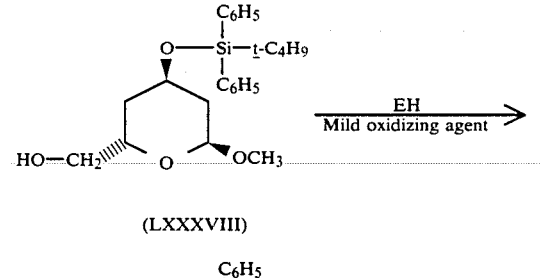
(LXXXVIII)
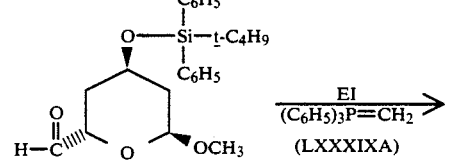
(LXXXIX)
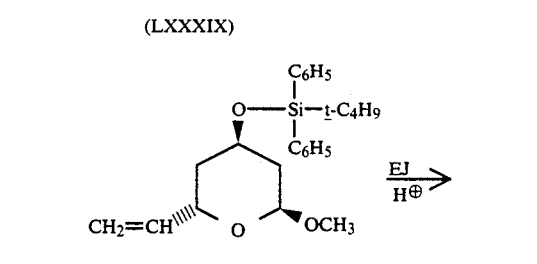
(XC)
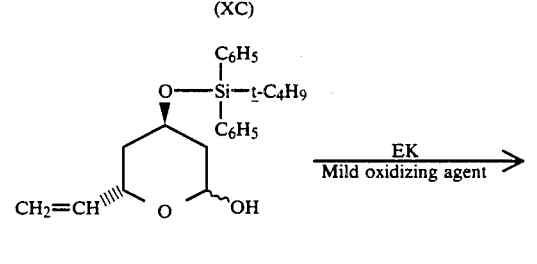
(XCI)
-continued
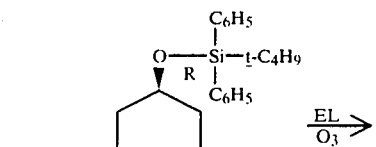
(XCII)
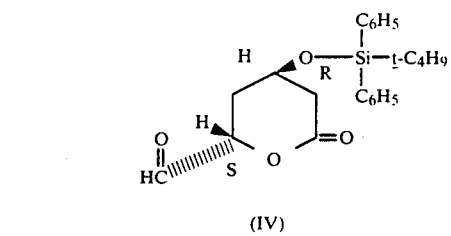
(IV)
REACTION SCHEME VIII
The compounds of Formula X may be synthesized by the following series of reactions:
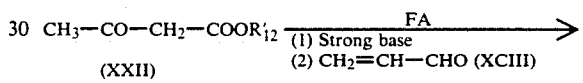
(XXII)
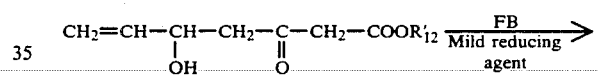
(XCIV)
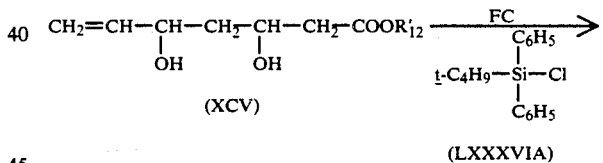
(XCV)
(LXXXVIA)
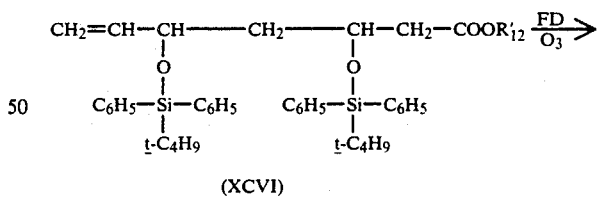
(XCVI)
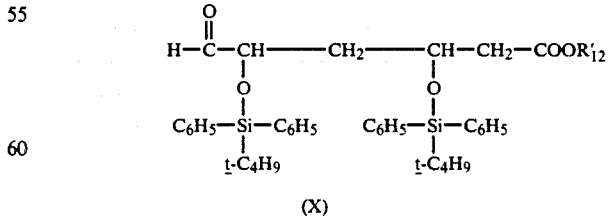
(X)
In the foregoing reaction schemes,
A is the anion of a pharmaceutically acceptable acid, Im is 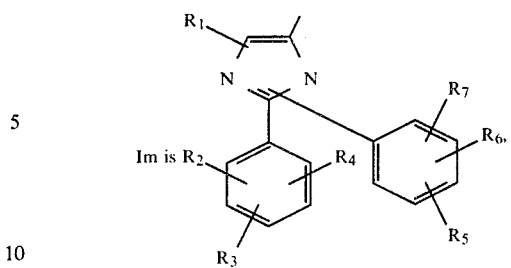
wherein $R_1-R_7$ are as defined above,
ImA and ImB are as defined in Reaction Schemes V and Vi,
each $R_{13}$ is independently $C_{1-3}$alkyl, preferably n-$C_{1-3}$alkyl and more preferably $C_{1-2}$alkyl, most preferably the three $R_{13}$'s in Formula XVIIA are identical,
Y is chloro or bromo,
$M_2^{\oplus}$ is sodium or potassium, and
$R_1-R_7$, $R_{12}$, $R_{12}'$ and M are as defined above.

| Reaction/Type | Reagents, Molar Ratios and Comments | Temperature | Time | Solvent | Inert Atmosphere |
|---|---|---|---|---|---|
| A | Excess triphenylphosphine, e.g., 2–10 moles per mole II. | 60° C.-reflux, pref. ≦150° C., esp. 75°–78° C. (in absolute ethanol) | 0.5–24 hrs. | AIO, pref. absolute ethanol | Yes |
| B (Wittig) | (1) 1–2 moles strong base, e.g., sodium hydride or pref. n-butyllithium (pref. as 1.3–1.7 M solution in hexane), per mole III. Pref., slowly and add n-butyl-lithium solution to solution of III. (2) 0.65–1.5 moles IV per mole III. Product (V) is a mixture of the (Z) and (E) (cis and trans, respectively) isomers which may be separated by chromatography. | −40°–5° C., pref. −35°– −20° C. −55°– −25° C., pref. −35°– −5° C. | 5–60 min. 0.75–18 hrs. pref. 1–4 hrs. | AIO, e.g. HC such as toluene or, pref., ES such as THF Same as Step 1 | Yes Yes |
| C (Deprotection) | 1–4 moles, pref. 2–4 moles, fluoride reagent, esp. tetra-n-butylammonium fluoride, per mole V and 1–2 moles, pref. 1.2–1.5 moles, glacial acetic acid per mole fluoride reagent. First add glacial acetic acid to solution of V, then add fluoride reagent. | 20°–60° C., pref. 20–25° C. | 2–30 hrs. | AIO, e.g., ES, pref. THF | — |
| D (Hydrogenation) | Excess hydrogen (more than 1 mole per mole V) and catalytic amount of platinum dioxide (e.g., 1–5 g. per mole V). Initial hydrogen pressure is conveniently 30–60 p.s.i. | 20°–25° C. | Until 1 mole hydrogen per mole V is taken up | Lower alkanol, e.g. ethanol | — |
| E (Deprotection) | Same as Reaction C (Molar quantities are per mole VII). | Same as C | Same as C | Same as C | — |
| F (Wittig) | Same as Reaction B. (Reactant in Step 2 is X.) Product (XI) is a mixture of the(Z) and (E) (cis and trans, respectively) isomers which may be separated by chromatography. | Same as B | Same as B | Same as B | Yes |
| G (Deprotection) | Same as Reaction C except utilize 2–8 moles, pref. 4–8 moles, fluoride reagent per mole XI. | Same as C | Same as C | Same as C | — |
| H (Hydrogenation) | Same as Reaction D (Molar quantities are per mole XI) | Same as D | Same as D | Same as D | — |
| I (Deprotection) | Same as Reaction C except utilize 2–8 moles, pref. 4–8 moles, fluoride reagent per mole XIII. | Same as C | Same as C | Same as C | — |
| J (Oxidation) | 5–60 moles, pref. 15–40 moles, manganese dioxide, pref. activated manganese dioxide, per mole XV. | 20° C.-reflux, pref. reflux, esp. refluxing toluene | 4 hrs.–9 days, pref. 6–16 hrs. in refluxing toluene | AIO, pref. HC or ES, esp. toluene, diethyl ether or THF or mixture of diethyl ether and THF | Yes |
| K (Wittig) | Alternative a: 1–2 moles, pref. 1.1–1.7 moles, XVII per mole XVI. | 80° C.-reflux, esp. refluxing toluene | 6–18 hrs. | AIO, pref. HC, esp. toluene | Yes |
| | Alternative b: (1) Synthesis of ylid: 1–1.05 moles strong base, pref. sodium hydride, per mole XVIIA. Pref., add small amount of XVIIA to suspension of sodium hydride in THF stirred at 20°–25° C., cool to −20°– −15° C. once reaction commences and complete addition and reaction at −20°– −15° C. | −20–25° C. | 1–2 hrs. | AIO, pref. ES, | Yes |
| | (2) 1–1.25 mole ylid from XVIIA (assuming 100% conversion of XVIIA to ylid) per mole XVI. Add solution of XVI to ylid solution at −20°– −15° C., allow to warm to 20°–25° C. and stir at this temperature for balance of reaction time. | −20°–25° C. | 6–18 hrs. | Same as Step 1 | Yes |
| L (Reduction) | (1) At least 2 equivalents of transferable hydride from a metal hydride reducing agent, e.g., lithium | 0°–25° C., pref. 0°–10° C. | 0.7–3 hrs., pref. 2 hrs. | AIO pref. ES, e.g., THF, or mixture of THF and toluene | Yes |

-continued

| Reaction/Type | Reagents, Molar Ratios and Comments | Temperature | Time | Solvent | Inert Atmosphere |
|---|---|---|---|---|---|
| M (Oxidation) | aluminum hydride or diisobutylaluminum hydride, per mole XVIII, pref. 3.8–6 moles diisobutylaluminum hydride per mole XVIII. (2) Quench with, for example, aqueous ammonium chloride solution. | 0°–25° C. | 1–5 min. | Same as Step 1 | — |
| N | Same as Reaction J (Molar quantities are per mole XIX). (p1) Preparation of cis-1-ethoxy-2-tri-n-butylstannyl-ethylene: 1 mole ethoxyacetylene and 1 mole tri-n-butyltin hydride. Add ethoxyacetylene to tri-n-butyltin hydride at 50° C. over 1 hr. period and stir at 50°–55° C. for 3 hrs. and at 60°–70° C. for 1 hr. | 20°–40° C. 50°–55° C. for 4 hrs. and 60°–70° C. for 1 hr. | 1–24 hrs. 5 hrs. | Same as J Neat | Yes Yes |
| | (p2) Preparation of XXI: 1–1.08 moles n-butyllithium and 1 mole cis-1-ethoxy-2-tri-n-butylstannylethylene. Add n-butyllithium (pref. as 1.3–1.7 M. solution in hexane) dropwise to solution of stannyl compound at −78° C. | −80°−−75° C. | 1–3 hrs, pref. 2 hrs. | AIO, e.g., ES, pref. THF | Yes |
| (Addition) | (1) 1–1.15 moles XXI (assuming 100% yield from Step (p2) per mole XVI. Crude enol ether product of this step may be used in next step without isolation and/or purification but isolation and purification of enol ether intermediate may improve yield of XX from next step. | −80°−−40° C., pref. −80°. | 1–8 hrs, pref. 1.5–5 hrs. | Same as Step (p2) | Yes |
| (Hydrolysis) | (2) Catalytic amount of p-toluenesulfonic acid or monohydrate thereof (e.g. 0.5–2 g, pref. 1.2–1.8 g, per mole XVI used in Step 1) and water. | 20°–40° C, pref. 20°–25° C. | 1–5 hrs, pref. 1.5–4 hrs. | Mixture of ES and water, pref. mixture of THF and water | — |
| O | (1) Generation of dianion of XXII: 1 mole XXII and 2–2.4 equivalents strong base, pref. 1–1.1 moles sodium hydride then 1–1.1 moles n-butyllithium or 2–2.2 moles lithium diisopropylamide. n-butyllithium is pref. employed as 1.3–1.7 M. solution in hexane and lithium diisopropylamide is prepared in situ from n-butyllithium and diisopropylamine. | −50°–10° C., pref. −20°–5° C. | 0.5–3 hrs. | AIO, e.g., ES, pref. THF | Yes |
| | (2) 1–2.5 moles, pref. 1.2–2.2 moles, more pref. 1.3–2 moles, dianion of XXII (assuming 100% conversion of XXII to its dianion) per mole XX. Product (XXIII) is racemic. | −80°–0° C., pref. −50°–0° C., more pref. −30°−−10° C. | 0.3–4 hrs.,pref. 0.3–1.5 hrs. | Same as Step 1 | Yes |
| | (3) Quench with, e.g., aqueous ammonium chloride solution (a) Non-stereoselective: 1–4, pref. 2–4, equivalents transferable hydride per mole XXIII, pref. sodium borohydride or complex of t-butylamine and borane. When a racemic XXIII is utilized, product (XXIV) is a mixture of all four possible stereoisomers (the erythro and threo racemates) wherein the ratio of the erythro stereoisomers to the threo stereoisomers is about 3.2–2.3. (b) Stereoselective: | Same as Step 2 −10°–30° C. | 1–5 min. 1–8 hrs. | Same as Step 1 IO, e.g., lower alkanol, esp. ethanol | — Yes |
| P (Reduction) | (1) 1–2 moles, pref. 1.02–2 moles, tri (primary or secondary $C_2$–$_4$alkyl)borane, pref.triethylborane or tri-n-butylborane, and, optionally, 0.5–8 liters, e.g., 0.75–6.5 liters, air (at 25° C. and 760 mm. Hg.) per mole XXIII. | 0°–50° C, pref. 0°–25° C. | 0.5–6 hrs, pref. 1–3.5 hrs. | AIO, pref. ES, esp. THF | — |
| | (2) 0.4–10 moles, pref. 1–10 moles, sodium borohydride per mole XXIII. After the reaction, quench reaction mixture with, for example, 10% hydrochloric acid and isolate crude | −100°−−20° C., pref. −90°−−70° C. | 2–96 hrs, pref. 12–72 hrs. | Same as Step 1 | — |

| Reaction/Type | Reagents, Molar Ratios and Comments | Temperature | Time | Solvent | Inert Atmosphere |
|---|---|---|---|---|---|
| | product by extracting with a suitable inert organic solvent (e.g., diethyl ether) and evaporating the solvent at reduced pressure. It is pref. to crystallize the cyclic boron ester, if possible. | | | | |
| | (3) Large excess of anhydrous methanol, e.g., 50-100 moles per mole XXIII. | 20°-40° C. pref. 2-4 | 0.7-5 hrs. | Neat | — |
| | (c) Alternative steroselective: | | | | |
| | (p) Preparation of zinc borohydride/diethyl ether: Add 1 mole zinc chloride to 5 l. anhydrous diethyl ether followed by 2 moles sodium borohydride. Stir for 16-18 hrs. and decant off the solution (a 0.15-0.2 M. solution of zinc borohydride in diethyl ether). N.B. The solid should be decomposed very carefully. | 20°-25° C. | 16-18 hrs. | Anhydrous diethyl ether | Yes |
| | (1) 1-6 moles zinc borohydride (in form of solution produced in Step p) per mole XXIII | −80°-−50° C., pref. −80°-−60° C. | 0.5-5 hrs., pref. 1-2 hrs. | AIO, pref. ES, esp. diethyl ether or mixture of diethyl ether with another ES | Yes |
| | (2) Add excess methanol, e.g., 10-100 moles per mole XXIII. | −80°-−25° C., pref. −80°-−75° C.→20°-25° C. | 1-2 hrs. | Same as Step 1 | — |
| | (3) Add water or excess dilute aqueous acetic acid to quench the reaction mixture or water followed by dilute aqueous acetic acid. | −80°-−25° C. NOTE: Warming to 20°-25° C. can be done after addition of methanol, water or dilute aqueous acetic acid | — | Same as Step 1 | — |
| | When a racemic XXIII is utilized in Alternative b or c, product (XXIV) is a mixture of the four possible stereoisomers wherein the ratio of the erythroisomers (racemate) to the threo isomers (racemate) is about 2-20:1, usually 5-15:1. Repeated recrystallization of the cyclic boron ester produced in Step 2 of Alternative b, if a solid, may raise the ratio or even yield pure erythroracemate and mother liquors enriched with the threo racemate. | | | | |
| Q (Hydrogenation) | Same as Reaction D (Molar qualities are per mole of XXIV) | Same as D | Same as D | Same as D | — |
| R (Hydrolysis) | 1-1.3 equivalents XXVI per mole XXV or, if it is desired to isolate XXVII, 0.93-0.99 equivalents XXVII per mole XXV. | 0° C.-reflux, pref. 0°-75° C., esp. 20°-70°C. | 1-4 hrs. | Inert aqueous organic, e.g. mixture of water and lower alkanol, pref. mixture of water and methanol or, esp., ethanol | — |
| S (Acidification) | At least 1 equivalent, e.g., 1-1.25 equivalents, acid, e.g. 2N. hydrochloric acid, per mole XXVII. | 0°-25° C. | 1-5 min. | Water or mixture of water and water miscible inert organic solvent, e.g., methanol, ethanol, diethyl ether or THF | — |
| T (Neutralization) | 0.95-0.99 equivalents,pref. 0.96-0.98 equivalents, XXIX per mole XXVIII. | 0°-25° C., pref. 20°-25° C. | 2-10 min. | Same as R | — |
| U (Lactonization) | Alternative a: Use of catalytic amount of strong acid such as p-toluenesulfonic acid is optional but usually omit. Use of Dean-Stark apparatus is pref. if solvent forms | 75° C.-reflux. pref. 75°-150° C., esp. 80°-120° C. | 3-18 hrs, pref. 4-7 hrs. | AIO, pref. HC, e.g., benzene, toluene or xylene or mixture thereof | — |

-continued

| Reaction/Type | Reagents, Molar Ratios and Comments | Temperature | Time | Solvent | Inert Atmosphere |
|---|---|---|---|---|---|
| | azeotrope with water<br>Alternative b:<br>1–1.5 moles of a lactonization agent, e.g., a carbodiimide, pref. a water-soluble carbodiimide such as N—cyclohexyl-N'—[2'-(N''—methylmorpholinium)ethyl]carbodiimide p-toluenesulfonate, per mole XXVIII.<br>Alternative b often results in higher yields of XXXI than Alternative a. Racemic erythro XXVIII yields racemic trans (lactone) XXXI, racemic threo XXVIII yields racemic cis (lactone) XXXI, mixture of racemic erythro and threo XXVIII yields mixture of racemic trans and cis (lactones) XXXI and single enantiomer of XXVIII yields single enantiomer of XXXI, e.g., 3R,5S erythro XXVIII yields 4R,6S trans XXXI. | 10–35° C., pref. 20–25° C. | 2–8 hrs., pref. 3–4 hrs. | AlO, pref. HLA, esp. methylene chloride | — |
| V (Esterification) | At least 2 moles, e.g., 2–10 moles, pref. 2.05–2.5 moles, XXXII per mole XXXI. | 0°–70° C., pref. 20°–25° C. | 2–12 hrs. | IO, e.g., ES such as THF or alcohol of the formula $R_{12}$—OH ($R_{12}$ same as in XXXXII), if a liquid same as R | — |
| W (Hydrolysis) | 1–1.3 equivalents XXVI per mole XXXI or, if it is desired to isolate XXVII, 0.95–1 equivalent, preferably 0.97–0.99 equivalent, XXVI per mole XXXI. Racemic trans (lactone) XXXI yields racemic erythro XXVII, racemic cic (lactone) XXXI yields racemic threo XXVII, mixture of racemic trans and cis (lactones) XXXI yields mixture of racemic erytho and threo XXXVII and single enantiomer of XXXI yields single enantiomer of XXVII, e.g., 4R,6S trans XXXI yields 3R,5S erythro XXVII. | 0° C.–reflux, pref. 0°–75° C., more pref. 20°–75° C., esp 40°–60° C. | 1–6 hrs, pref. 1–4 hrs. | Same as R | — |
| X (Acidification) | 1 equivalent XXXIV per mole XXXIII. If XXXIV is a gas such as hydrogen chloride, can bubble excess XXXIV through solution of XXXII. | 0°–25° C., pref. 20°–25° C. | 1–15 min. | IO, pref. lower alkanol, e.g. methanol or ethanol or ES e.g., diethyl ether | — |
| Y (Acidification) | Same as Reaction X (Molar quantities are per mole XXXI). | Same as X | Same as X | Same as X | — |
| Z (Acidification) | Same as Reaction X (Molar quantities are per mole XXVIII). | Same as X | Same as X | Same as X | — |
| AA (Acylation) | 1–1.5 moles, pref. 1.1–1.3 moles. XLII and 2–2.5 equivalents of a base such as sodium hydroxide per mole XLI. Simultaneously add solution of XLII and base to basic solution of XLI. Reaction mixture must be basic at all times. Combine reactants at −5°–5° C. and then, if desired, reaction mixture may be allowed to warm to 20°–25° C. After the reaction, acidify with, for example, concentrated sulfuric or hydrochloric acid.<br>Alternative a: | −5°–5° C. → 20°–25° C. | 1–4 hrs. | Mixture of ES, pref. dioxane, and water | — |
| AB | 2–4 moles, pref. 3 moles, acetic anhydride, 1–3 moles, pref. 2–2.2 moles, 20°–25° C.of an organic base, pref. 2 moles of a tri-($C_{1-3}$alkyl)amine, e.g., triethylamine, and catalytic amount, e.g., 0.1 mole, of 4-dimethylaminopyridine, per mole XLIII. After the reaction, quench mixture with, for example, methanol at 0°–5° C.<br>Alternative b: | 15°–30° C., pref. | 12–24 hrs. | Neat | Yes |
| AC | Same as Reaction BC (Molar quantities are per mole XLIII). 1–5 moles XLV and catalytic amount (e.g., 0.1–5 g.) of p-toluenesulfonic acid mono- | Same as BC 80° C.–reflux, pref. 100–111° C. | Same as BC 24–72 hrs. | Same as BC AIO, pref. HC, e.g. benzene or toluene | Yes<br>Yes |

| Reaction/Type | Reagents, Molar Ratios and Comments | Temperature | Time | Solvent | Inert Atmosphere |
|---|---|---|---|---|---|
| | hydrate per mole XLIV. Pref. use Dean-Stark apparatus if solvent forms azeotrope with water. | | | | |
| AD | 1.5–3 moles, pref. 1.9–2.1 moles, phosphorus pentachloride per mole XLVI. Combine reactants at −30°–15° C., allow to warm to 20°–25° C. and maintain at this temperature for balance of reaction time. Quench reaction mixture at 0°–25° C. with water and then make basic with, for example 10% sodium hydroxide solution. | −30°–−15° C.→ 20°–25° C. | 16–72 hrs. | HLA, pref. chloroform | Yes |
| AE | 1–2.1 moles lead tetraacetate and, pref., catalytic amount (0.5–2 g.) of benzoyl peroxide per mole XLVII. Generally, use of benzoyl peroxide and glacial acetic acid permits use of reaction times at lower end of the indicated range; the reaction temperature must usually be at least 50° C. when no benzoyl peroxide is used. | 20°–80° C. | 1.5–16 hrs. | Glacial acetic acid or HC such as benzene | — |
| AF (Hydrolysis) | 1–6 equivalents of a base, pref. sodium hydroxide or potassium hydroxide, per mole XLVIII. | 20°–50° C. | 2–24 hrs. | Same as R | — |
| AG (Halogenation) | 2–8 moles thionyl chloride per mole XLIX. | 0°–80° C. | 2–18 hrs. | Neat | — |
| BA | (1) Combine 1 1. saturated aqueous ammonium hydroxide, 1.9–2.1 moles lithium chloride, 5.9–6.1 moles potassium hydroxide and 1–1.02 moles benzyltriethylammonium chloride per mole LI to be used in Step 3. See Step 1 of Example 3. | 20°–25° C. | — | Mixture of water and HLA, pref. methylene chloride | Yes |
| | (2) Bubble ammonia in for 30 min. | 0° C. | 30 min. | Same a Step 1 | Yes |
| | (3) Add LI and additional gaseous ammonia portionwise over period of 1 hr. | 0° C. | 1 hr. | Same as Step 1; pref. mixture of water methylene chloride and chloroform | |
| | (4) Bubble in additional ammonia for 5 hrs. | 0° C. | 5 hrs. | Same as Step 3 | Yes |
| | (5) Stir. | 20°–25° C. | 8–24 hrs. | Same as Step 3 | Yes |
| | (6) Acidify to pH 6.5 with, for example, concentrated hydrochloric acid. Product (LII) is racemic. | 20°–25° C. | 1–5 min. | Water | — |
| BB (Acylation) | Same as Reaction AA (Molar quantities are per mole LII). Alternative a: | Same as AA | Same as AA | Same as AA | Yes |
| BC | (1) 2–6 moles, pref. 3–5 moles, acetic anhydride 4–6 moles of an organic base, pref. pyridine, and catalytic amount, e.g., 0.005–0.1 mole, of 4-dimethylaminopyridine per mole LIII. (2) Add solvent and heat. Alternative b: | 20°–25° C. 100°–130° C. | 0.5–1.5 hrs. 2–4 hrs. | Neat Glacial acetic acid | Yes |
| BD | Same as Reaction AB (Molar quantities per mole LIII) Alternative a: | Same as AB | Same as AB | Same as AB | Yes |
| | 10–20 moles LV, 30–50 moles of dehydrating agent such as magnesium sulfate and a catalytic amount (e.g., 0.5–5 g.) of p-toluenesulfonic acid monohydrate per mole LIV. Alternative b: | 20°–40° C. | 4–6 days | AlO, pref. mixture of HLA and HC, esp. mixture of methylene chloride and benzene | Yes |
| BE | Same as Reaction AC (Molar quantities are per mole LIV). | Same as AC | Same as AC | Same as AC | Yes |
| BF | Same as Reaction AD (Molar quantities are per mole LVI). | Same as AD | Same as AD | Same as AD | Yes |
| BG (Hydrolysis) | Same as Reaction AE (Molar quantities are per mole LVII). | Same as AE | Same as AE | Same as AE | Yes |
| BH (Halogenation) | Same as Reaction AF (Molar quantities are per mole LVIII). | Same as AF | Same as AF | Same as AF | — |
| | Same as Reaction AG (Molar quantities are per mole LIX). | Same as AG | Same as AG | Same as AG | — |

-continued

| Reaction/Type | Reagents, Molar Ratios and Comments | Temperature | Time | Solvent | Inert Atmosphere |
|---|---|---|---|---|---|
| EA | (1) Catalytic amount of sodium, e.g., 0.026 mole per mole LXXXI. Add sodium to methanol, stir for 15 min., add LXXXI portionwise over 15 min. period and stir for 1 hr. | 20°–25° C. | 1.5 hrs. | Methanol | Yes |
| EB | (2) 1–1.01 moles mercuric acetate per mole LXXXI. | 20°–25° C. | 5 hrs. | Methanol | Yes |
|  | (1) 1.55–1.6 moles sodium chloride per mole LXXXII. | 20°–25° C. | 30 min. | Methanol | Yes |
|  | (2) 1–1.1 moles, esp. 1.08 moles, sodium borohydride per mole LXXXII. Add sodium borohydride portionwise over 1.5 hr. period at 0°–5° C. Add isopropanol after each portion (in amounts such that final solvent is 3:2 mixture of methanol and isopropanol) and stir at 20°–25° C. for 3.5 hours. | –5°–0° C. → 20°–25°C. | 5 hrs. | 3:2 mixture of methanol and isopropanol | Yes |
| EC (Etherification) | 0.8–1 mole, pref. 0.84 mole, triphenylmethyl chloride per mole LXXXIII. Add triphenylmethyl chloride portionwise over 15 min. period at 20°–25° C. and stir at 20°–25° C. for 1 hr. and at 35°–40° C. for 30–31 hrs. | 35°–40° C. | 30–32 hrs. | 10–15:1, pref. 12–14:1, mixture of pyridine and methylene chloride | Yes |
| ED | (1) 4–5 moles, pref. 4.75 moles, sodium hydride per mole LXXXIV. Over 30 min. period add solution of LXXXIV in THF to sodium hydride stirred in THF (some cooling is necessary to maintain temperature at 25°–30° C.) and stir at 20°–25° C. for 3 hrs. | 20°–30° C. | 3.5 hrs. | Hexamethylphosphoramide or, pref., dry THF | Yes |
|  | (2) 1 mole of LXXXIVA per mole LXXXIV. Over 30 min. period add solution of LXXXIVA to reaction mixture stirred at –30° C. and allow reaction mixture to slowly warm to 20°–25° C. over 2 hr. period. | –30° C. → 20°–25° C. | 2.5 hrs. | Same as Step 1 | — |
| EE (Reduction) | 1.8–1.9 moles, pref. 1.85 moles, lithium aluminum hydride per mole LXXXV. Over 1.5 hr. period add lithium aluminum hydride to solution of LXXXV stirred at –10°–0° C. and stir at –10°–10° C. for 15–17 hrs. | –10°–10° C. | 16.5–18.5 hrs. | Dry methyl t-butyl ether or diethyl ether | Yes |
| EF (Silylation) | 1–2 moles, pref. 1.1 moles, LXXXVIA per mole LXXXVI and 2 moles imidazole per mole LXXXVIA. Add LXXXVIA to solution of LXXXVI and imidazole over 30 min. period (maintain maximum temperature of 32° C.) and stir for 15.5–18.5 hrs. at 20°–25° C. | 20°–32° C. | 16–19 hrs. | Dry dimethylformamide | Yes |
| EG (Hydrolysis) | 125–130 ml. 70% (v/v) aqueous trifluoroacetic acid per mole LXXXVII. Over 1 hr. period add aqueous trifluoroacetic acid dropwise to solution of LXXXVII stirred at –55°–50° C., allow to warm to –10° C. over 1 hr. period and stir at –10°–0° C. for 3 hrs. | –55°– –50° C. → –10°–0° C. | 5 hrs. | Methylene chloride | Yes |
| EH (Oxidation) | 2 moles pyridinium chlorochromate or 6–10 moles pref. 8 moles, chromium trioxide (pref. complexed with pyridine, more pref. 2 moles pyridine per mole chromium trioxide) (pref. 4Å size) per mole LXXXVIII. When pyridinium chlorochromate is used, add it portionwise over 15–30 min. period to balance of reaction mixture, and when chromium trioxide is used, add solution of LXXXVIII to balance of reaction mixture over 15–30 min. period and, in each case, stir for 2–3 hrs. | 20°–25° C. | 2.25–3.5 hrs. | Dry methylene chloride | Yes |
| EI (Wittig) | (p) Synthesis of LXXXIXA: 1 mole methyltriphenylphosphonium bromide or, preferably, iodide and 1–1.03 moles n-butyllithium. Add solution of n-butyllithium, pref. 1.3–1.7 M. in hexane, dropwise over 10–20 min. | –30°–25° C., pref. –5°–5° C. | 1.16–1.33 hrs. | Dry THF | Yes |

-continued

| Reaction/Type | Reagents, Molar Ratios and Comments | Temperature | Time | Solvent | Inert Atmosphere |
|---|---|---|---|---|---|
| | period to slurry of phosphonium compound and stir for 1 hr. (1) 1-1.5 moles, pref. 1.1-1.45 moles, LXXXIXA per mole LXXXIX. Add solution of LXXXIX in dry THF dropwise over 30 min. period to product of Step p stirred at $-10°$-$10°$ C., allow reaction mixture to warm to $20°$-$25°$ C. and stir for balance of reaction time. | $-10°$-$10°$ C., pref. $-5°$-$5°$ C. $\rightarrow 20°$-$25°$ C. | 16-19 hrs. | Dry THF | Yes |
| EJ (Hydrolysis) | Heat XC in large excess of the solvent. Pref., quantity of solvent is such that reaction mixture contains 40-60 moles acetic acid per mole XC. | $60°$-$70°$ C. | 2-3 hrs. | Mixture of glacial acetic acid, THF and water, pref. a 3:2:2 mixture | — |
| EK (Oxidation) | 2-4 moles pyridinium chlorochromate per mole XCI. | $20$-$25°$ C. | 16-24 hrs., pref. 17-19 hrs. | Dry methylene | — |
| EL (Ozonolysis) | Excess ozone. Bubble ozone through solution of XCII until a bluish coloration persists and then quench reaction mixture with dimethyl sulfide or triphenylphosphine | $-80°$-$70°$ C., pref. $-78°$ C. | 2-30 min. | $C_1$-$_3$alkanol, esp. methanol or HLA, esp. methylene chloride, or ethyl acetate | — |
| FA | (1) Generation of dianion of XXII: 1 mole XXII and 2-2.2 equivalents strong base, e.g., 2-22 moles lithium diisopropylamide or, pref., 1-1.1 moles sodium hydride followed by 1-1.1 moles n-butyllithium (pref. as 1.3-1.7 M. solution in hexane). (2) 1-1.2 moles dianion of XXII (assuming 100% conversion of XXII to its dianion) per mole XCIII. Slowly add solution of XCIII in, pref., dry THF to solution of dianion stirred at $-80°$-$0°$ C., pref. $-40°$-$-20°$ C., esp. $-35°$-$-30°$ C., stir at same temperature for 30 min. and allow to warm to $20°$-$25°$ C. over a 2 hr. period. Product (XCIV) is a racemate. (a) Non stereoselective: | $-50°$-$10°$ C., pref. $-10°$-$10°$ C. $-80°$-$0°$ C., pref. $-40°$-$-20°$ C., esp. $-35°$-$-30°$ C., $\rightarrow 20°$-$25°$ C. | 0.3-1.5 hrs. pref. 0.5-1 hr. 2.5 hrs. | AIO, e.g., ES, pref. THF Same as Step 1 | Yes Yes |
| FB (Reduction) | Same as Reaction P, Alternative a (Molar quantities are per mole of XCIV). Product (XCV) is a mixture of all four possible stereoisomers (the erythro and threo racemates), the erythro to threo ratio being approximately 3:2 to 2:3. (b) Stereoselective: | Same as P, a | Same as P, a | Same as P, a | Yes |
| | (1) 1-1.25 moles, pref. 1.05-1.25 moles, esp. 1.2-1.25 moles, tri-(primary or secondary $C_2$-$_4$alkyl)borane, pref. triethylborane or tri-n-butylborane, esp. the latter, per mole XCIV. Use of air as in Step 1 of Alternative b of Reaction P is optional. | $0°$-$50°$ C., pref. $20°$-$25°$ C. | 1-6 hrs, pref. 1.5-3 hrs. | AIO, pref. ES, esp. THF | — |
| | (2) 0.4-1.5 moles, pref. 1-1.25 moles, sodium borohydride per mole XCIV. After the reaction, reaction mixture is quenched with, for example, 10% hydrochloric 10% hydrochloric acid and crude product is isolated by extraction with, for example, diethyl ether and evaporation of the solvent. | $-100°$-$-40°$ C., pref. $-90°$-$70°$ C., esp. $-90°$-$-78°$ C. | 2-60 hrs., pref. 24-48 hrs. | Same as Step 1 | — |
| | (3) Large excess of methanol (e.g., 50-100 moles per mole XCIV) or mixture of methanol (e.g., 10-20 l. per mole XXIV), hydrogen peroxide (e.g., 4-8 l. of 30% aqueous hydrogen peroxide per mole XCIV) and a pH 7-7.2 aqueous phosphate buffer (pref. 6-10 l. of a pH 7 aqueous phosphate buffer (e.g. 0.054 M. sodium, 0.024 M. potassium and 0.047 M. phosphate) per mole XCIV). The amount of buffer must be sufficient to maintain a pH of 7-7.2. Dissolve | $0°$-$25°$ C., pref. $0°$-$10°$ C., when using a mixture of methanol, hydrogen peroxide and buffer and °-$60°$ C. when using methanol alone | 0.7-5 hrs., pref. 2-4 hrs. | As indicated | — |

-continued

| Reaction/Type | Reagents, Molar Ratios and Comments | Temperature | Time | Solvent | Inert Atmosphere |
|---|---|---|---|---|---|
| FC (Silylation) | product of Step 2 in methanol and add buffer and aqueous hydrogen peroxide. Use of methanol alone is preferred. (c) Alternative stereoselective: Same as Reaction P, Alternative c 2-8 moles, pref. 4 moles, LXXXVIA per mole XCV and 2 moles imidazole per mole LXXXXVIA. Slowly add LXXXVIA to solution of XCV and imidazole (at rate such that temperature does not exceed 30° C.) and stir at, pref., 20°-25° C. for balance of reaction time. | Same as P, c 20°-30° C., pref. 20°-25° C. | Same as P, c 16-19 hrs. | Same as P, c Dry dimethyl-formamide | Same as P, c Yes |
| FD (Ozonolysis) | Same as Reaction EL | Same as EL | Same as EL | Same as EL | — |

In the preceding table,
AtO = anhydrous inert organic solvent
ES = ether solvent, for example, diethyl ether, 1,2-diethoxyethane, 1,2-dimethoxyethane, tetrahydrofuran, dioxane and mixtures thereof
esp. = especially
HC = hydrocarbon solvent, for example, benzene, toluene, xylene and mixtures thereof
HLA = halogenated lower alkane solvent, for example, carbon tetrachloride, chloroform, 1,1-dichloroethane, 1,2-dichloroethane, methylene chloride and 1,1,2-trichloroethane, usually preferably methylene chloride
hr. (hrs.) = hour(s)
IO = inert organic solvent
min. = minutes
pref. = preferably, preferred
THF = tetrahydrofuran Most of the molar amounts (ratios) given in the preceding table are merely exemplary and may be varied, as is evident to one of ordinary skill in the art. For example, in a reaction of two compounds one of which is readily available and one of which isn't, an excess of the readily available compound may be used to drive the reaction further towards completion (unless the use of an excess would increase the synthesis of an undesired compound).

Likewise, most of the temperature ranges given in the preceding table are merely exemplary, and it is within the ability of one of ordinary skill in the at to vary those that are not critical.

The reaction times set forth in the preceding table are also merely exemplary and may be varied. As is well-known, the reaction time is often inversely related to the reaction temperature. Generally, each reaction is monitored by, for example, thin layer chromatography and is terminated when at least one starting material is no longer present, when it appears that no more of the desired product is being formed, etc.

Conventional work-up procedures have generally been omitted from the preceding table.

As utilized in the preceding table, the term "solvent" embraces mixtures of solvents and implies that the reaction medium is a liquid at the desired reaction temperature. It should, therefore, be understood that not all of the solvents listed for a particular reaction may be utilized for the entire recited temperature range. It should also be understood that the solvent must be at least substantially inert to the reactants employed, intermediates generated and end products under the reaction conditions utilized.

The term "inert atmosphere", as utilized in the preceding table, means an atmosphere that does not react with any of the reactants, intermediate or end products or otherwise interfere with the reaction. While a carbon dioxide atmosphere is suitable for certain reactions, the inert atmosphere is usually nitrogen, helium, neon, argon or krypton, or a mixture thereof, and most often dry nitrogen to maintain anhydrous conditions. Most reactions, including those where the use of an inert atmosphere is not specified, are carried out under an inert atmosphere, usually dry nitrogen, for convenience.

Reactions analogous to Reactions A-C, E-G, I-P, T-V, AG and BH are described in detail in copending application Ser. No. 06/722,288, filed by Faizulla G. Kathawala on Apr. 11, 1985 and titled Indole Analogs of Mevalonolactone and Derivatives thereof. These reactions may be carried out analogously to the corresponding reactions of said application. Also disclosed in said application are Reactions EA-EH of this application. Said application, particularly pages 14-21, 24-26, 28-52, 65-76, 82-96, 98-102, 106, 107 and 116-122 thereof, is hereby incorporated by reference. Generally, where the reaction conditions set forth in said application differ from those set forth in this application, the reaction conditions set forth in said application may also be utilized for the compounds of this application.

Reactions EA-EF and EI-EL are described in further detail in U.S. Pat. No. 4,625,039. Also described in said patent is an alternate procedure for carrying out Reactions EG and EH. Said patent, particularly column 9, line 26–column 16, line 67 thereof, is hereby incorporated by reference.

Reactions FA-FD are described in further detail in abandoned application Ser. No. 06/596,411, filed by me and Charles F. Jewell, Jr. on Apr. 3, 1984 and titled Preparation of Olefinic Compounds. Said application, particularly pages 16–19 thereof, is hereby incorporated by reference.

The product of each reaction may, if desired, be purified by conventional techniques such as recrystallization (if a solid), column chromatography, preparative thin layer chromatography, gas chromatography (if sufficiently volatile), fractional distillatin under high vacuum (if sufficiently volatile) or high pressure (performance) liquid chromatography (HPLC). Often, however, the crude product of one reaction may be employed in the following reaction without purification.

Some of the reactions described above may yield mixtures of two or more products only one of which leads to the desired compound of Formula I. For example, Reactions AE and BF may yield mixtures when, for example, at least one of $R_2$-$R_7$ is primary or secondary alkyl, particularly methyl. Any obtained mixture may be separated by conventional techniques such as those set forth in the preceding paragraph.

As is evident to those in the art, each of the compounds of Formulae XXIII, XLI, XLIII, XLIV, XLVI, LII, LIII, LIV, LVI and XCIV has a single center of asymmetry and, therefore, may be resolved into two optically active isomers. When a compound of Formula XXIII or XCIV is converted into a compound of Formula XXIV or XCV, respectively, an additional center of asymmetry is generated. Consequently, when a racemic compound of Formula XXIII or XCIV is utilized, four stereoisomers (two pairs of diastereoisomers) of the resulting compound of Formula XXIV or XCV are formed, whereas when an optically pure compound of Formula XXIII or XCIV is utilized, two diastereoisomers of the compound of Formula XXIV or XCV are formed. The center of asymmetry of each compound of Formulae XLI, XLIII, LII, LIII, etc. may be ignored since it is destroyed in Reaction AD or BE, as the case may be.

The compounds of Formulae I (including those of Formulae IA, IB, XII, XIV, XXV, XXVII, etc.), the pharmaceutically acceptable acid addition salts thereof, X, XI, XIII, XCV and XCVI have two centers of asymmetry and, therefore, may exist in four stereoisomeric forms. Except where the compound is formed from an optically pure precursor already having both chiral carbon atoms or where the reaction involves the use of a stereospecific reagent that gives an optically pure product, the compound is obtained as a mixture of two (if formed from an optically pure compound having one center of asymmetry) or four (if formed from a racemic compound having one center of asymmetry) stereoisomers.

The obtained mixtures of stereoisomers may be separated by conventional means. For example, diastereoisomers may be separated by fractional crystallization, column chromatography, preparative thin layer chromatography and HPLC. Each mixture of four stereoisomers of a compound of Formula XXXI may, for example, be separated by HPLC into its cis and trans (lactone) components, each of which is a racemate that may be resolved into two optically active enantiomers.

Techniques for separating a racemate into its two optically active enantiomers are known. For example, a racemic compound having a carboxylic acid group may be reacted with an optically pure organic base having at least one center of asymmetry to form a mixture of diastereoisomeric salts that may be separated by fractional crystallization, column chromatography, etc. or it may be reacted with an optically pure alcohol having at least one center of asymmetry to form a mixture of diastereoisomeric esters which may be separated by conventional techniques such as those set forth above or below. Likewise, a racemic compound having a carboxylic acid, acyl halide, ester or lactone group may be reacted with an optically pure organic base, i.e., an amine, to form a mixture of diastereoisomeric amides that may be separated by conventional means, e.g., fractional crystallization, column chromatography and/or HPLC. For example, a racemic lactone of Formula XXXI may be reacted with an excess of R-(+)-α-methylbenzylamine (or the corresponding S-(−) compound) to form a mixture of two diastereoisomeric α-methylbenzylamides which may be separated by, for example, column chromatography on a silica gel column and/or by HPLC using a Partisil column. Often it is desirable to utilize both techniques, i.e., to partially separate the diastereoisomers by column chromatography and to purify each fraction by HPLC. Typically, the α-methylbenzylamides are synthesized by reacting the racemic lactone with a large molar excess of the amine at 20°–25° C. for 16–24 hours. The reaction is run neat, with the excess amine serving as the solvent. After the reaction, the excess amine is removed by vacuum distillation at 25°–35° C. After separation, each chiral amide may be hydrolyzed to the corresponding, for example, sodium, salt by, for example, refluxing with 1.5–3, preferably 2–2.2, equivalents of a base such as sodium hydroxide for 5–25 hours in a mixture of water and ethanol. The resulting salts may be converted to the corresponding free acids, esters, lactones and other salts by conventional means such as the reactions set forth in Reaction Scheme IV. On the other hand, a racemic compound having a hydroxy group may be esterified with an optically pure carboxylic acid having at least one center of asymmetry to form a mixture of diastereoisomeric esters or it may be reacted with an optically pure trisubstituted silyl halide, e.g., (−)-α-naphthylphenylmethylchlorosilane (Sommer et al., J. Am. Chem. Soc. 80, 3271 (1958).), to form a mixture of two diastereoisomeric silyloxy compounds, which mixture may be separated by conventional techniques. For example, diastereoisomeric (−)-α-naphthylphenylmethylsilyl derivatives of a lactone of Formula XXXI may be separated on a silica column having covalently bound L-phenylglycine. After separation, the optically pure salts, amides, esters or silyloxy compounds are reconverted to the corresponding carboxy group- or hydroxy group-containing compounds with retention of optical purity. For example, the process conditions disclosed for Reactions C, E, G and I may be utilized to cleave (−)-α-naphthylphenylmethylsilyl and other silyl groups.

The compounds of Formulae XVII, XVIIA, XXII, XXVI, XXIX, XXXII, XLI, XLII, XLV, LI, LV, LXXXI–LXXXVIII and XCIII and the reagents not designated by a Roman numeral are known or, if unknown, may be synthesized by processes analogous to those described in the literature for similar known compounds. For example, Compound LXXXI is commercially available tri-O-acetyl-D-glucal and Compounds LXXXV–LXXVIII are disclosed in Yang et al., Tetrahedron Letters 23, 4305–4308 (1982).

A preferred process for the synthesis of the erythro racemate of the compound of Formula X wherein $R_{12}'$ is methyl is disclosed in Kapa, Tetrahedron Letters 25, 2435–2438 (1984). The other compounds of Formula X in racemic erythro form may be synthesized similarly. See also U.S. Pat. No. 4,571,428. Said patent, particularly column 3, line 28–column 6, line 23 and column 7, line 40–column 10, line 68 thereof, is hereby incorporated by reference.

Since any compound of Formula I wherein Z is a group of Formula a wherein $R_{11}$ is a cation other than M may be converted into the corresponding compound wherein $R_{11}$ is hydrogen, M or $R_{12}$ by the processes of Reaction Scheme IV, the compounds of Formula I wherein Z is a group of Formula a and $R_{11}$ is a pharmaceutically unacceptable cation are also within the scope of this invention since they are useful as intermediates. However, such compounds are not compounds of Formula I as utilized in this application, except where indicated to the contrary.

Also within the scope of this invention are the intermediates of Formulae V, VII, XI, XIII, XVI, XVIII–XX and XXIII. The preferences for each variable are the same as those set forth for the compounds of Formula I, with the preferred groups of such compounds including those that correspond to Groups (i)–(xviii) (for Formulae XI, XIII, XVI, XVIII–XX and XXIII) and Groups (xix)–(xxvii) (for Formulae V and VII) to the extent consistent therewith.

Besides having the utility set forth below, every compound of Formula I is useful as an intermediate in the synthesis of one or more other compounds of Formula I utilizing the reactions set forth in Reaction Scheme IV.

The compounds of Formula I and the pharmaceutically acceptable acid addition salts thereof are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Their biological activity may be demonstrated in the following two tests:

Test A. In Vitro Microsomal Assay of HMG-CoA Reductase Inhibition:

200 μl. aliquots (1.08–1.50 mg./ml.) of rat liver microsomal suspensions, freshly prepared from male Sprague-Dawley rats (150–225 g. body weight), in Buffer A with B 10 mmol. dithiothreitol are incubated with 10 μl. of a solution of the test substance in dimethylacetamide and assayed for HMG-CoA reductase activity as described in Ackerman et al., J. Lipid Res. 18, 408–413 (1977), the concentration of the test substance in the assay system being 0.0005–2,000 μmolar. In the assay the microsomes are the source of the HMG-CoA reductase enzyme which catalyzes the reduction of HMG-CoA to mevalonate. The assay employs a chloroform extraction to separate the product, [$^{14}$C]mevalonolactone, formed by the HMG-CoA reductase reduction of the substrate, [$^{14}$C]HMG-CoA. [$^3$H]mevalonolactone is added as an internal reference. Inhibition of HMG-CoA reductase is calculated from the decrease in specific activity ([$^{14}$C/$^3$H]mevalonate) of test groups compared to controls.

The IC$_{50}$ is the concentration of the test substance in the assay system calculated or observed to produce a 50% inhibition of HMG-CoA reductase activity.

Test B. In Vivo Cholesterol Biosynthesis Inhibition Test:

In vivo studies utilize male Wistar Royal Hart rats weighing 150±20 g. which have been kept for 7–10 days on an altered light cycle (6:30 A.M.–6:30 P.M.

dark) housed two per cage and fed powdered Purina Rat Chow and water ad libitum. Three hours before the diurnal maximum of cholesterol synthesis at mid-dark, the rats are administered orally the test substance (e.g., 0.005–200 mg./kg. body weight) dissolved or as a suspension in 0.5% carboxymethylcellulose in a volume of 1 ml./100 g. body weight. Controls receive vehicle alone. One hour after receiving the test substance (or the vehicle alone), the rats are injected intraperitoneally with about 25 μCi/100 g. body weight of sodium [1-$^{14}$C]acetate 1-3 mCi/mmol. Two hours after mid-dark, blood samples are obtained under sodium hexobarbitol anesthesia, and the serum is separated by centrifugation.

Serum samples are saponified and neutralized, and the 3β-hydroxysterols are precipitated with digitonin basically as described in Sperry et al., J. Biol. Chem. 187, 97 (1950). The [$^{14}$C]digitonides are then counted by liquid scintillation spectrometry. After correcting for efficiencies, the results are calculated in nCi (nanocuries) of 3β-hydroxysterol formed per 100 ml. of serum. Inhibition of 3β-hydroxysterol synthesis is calculated from the reduction in the nCi of 3β-hydroxysterols formed from test groups compared to controls.

The $ED_{50}$ is the dose of the test substance calculated or observed to produce a 50% inhibition of 3β-hydroxysterol synthesis.

Since they inhibit cholesterol biosynthesis, the compounds of Formula I and the pharmaceutically acceptable acid addition salts thereof (including those of each subgroup thereof) are useful for lowering the blood cholesterol level in animals, e.g., mammals, especially larger primates, in particular humans, and, therefore, as hypolipoproteinemic and anti-atherosclerotic agents.

The precise dosage of the compound of Formula I or the pharmaceutically acceptable acid addition salt thereof to be employed for inhibiting cholesterol biosynthesis depends upon several factors including the host, the nature and the severity of the condition being treated, the mode of administration and the particular active substance employed. However, in general, suitable oral daily dosages of the compounds of Formula I and the pharmaceutically acceptable acid addition salts thereof for the satisfactory inhibition or reduction of cholesterol biosynthesis (i.e., the satisfactory reduction of the blood cholesterol level and satisfactory treatment of hyperlipoproteinemia and atherosclerosis) are indicated to be 0.01–100 mg./kg. body weight, e.g., 0.01–10 mg./kg. body weight for the more active compounds. For most larger primates such as humans, a suitable oral daily dosage is indicated to be 0.5–2000 mg., e.g., 0.5–200 mg. for the more active compounds. For administration by injection, a dosage somewhat lower than would be used for oral administration of the same active substance to the same host having the same condition is usually employed. However, the above dosages are also typically used for i.v. administration.

The daily dosage may be administered in a single dose but more typically is administered in two to four equal portions, typical doses being 0.25–2000 mg. Often, a small dosage is administered initially, and the dosage is gradually increased until the optimal dosage for the host under treatment is determined.

A typical dosage unit for oral administration may contain 0.125–500 mg. of a compound of Formula I or a pharmaceutically acceptable acid addition salt thereof.

The compounds of Formula I and the pharmaceutically acceptable acid addition salts thereof may be formulated into conventional pharmaceutical compositions and administered by any conventional mode of administration, in particular enterally, e.g., in the form of capsules or tablets, or parenterally, e.g., in the form of sterile injectable solutions or suspensions. The pharmaceutical compositions comprise a compound of Formula I or a pharmaceutically acceptable acid addition salt thereof and at least one pharmaceutically acceptable solid or liquid carrier (or diluent). They may be formulated in conventional manner. The compounds and pharmaceutically acceptable acid addition salts of each subgroup thereof may likewise be formulated into such pharmaceutical compositions and administered by such routes.

The compounds of Formula I and the pharmaceutically acceptable acid addition salts thereof (including those of each subgroup thereof) may be formulated into such pharmaceutical compositions containing an amount of the active substance that is effective for inhibiting cholesterol biosynthesis in unit dosage form and such compositions comprising at least one solid pharmaceutically acceptable carrier.

The preferred compound of this invention, that of Example 2, exhibited an $IC_{50}$ in Test A of 0.0026 μmolar whereas that of Compactin was 0.77 μmolar and that of Mevinolin was 0.14 μmolar in this test. Other tested compounds of this invention exhibited $IC_{50}$'s of 0.0017–1.31 μmolar in this test. In Test B the compound of Example 2 exhibited an $ED_{50}$ of 0.026 mg./kg. whereas that of Compactin was 3.5 mg./kg. and that of Mevinolin was 0.41 mg./kg. The daily dosage for the compound of Example 2 is, therefore, indicated to be 0.5–150 mg., preferably 1–20 mg., for most larger primates such as humans.

A representative formulation suitable for encapsulation in a hard gelatin capsule by conventional techniques is:

| | |
|---|---|
| Compound of Formula I, e.g., the compound of Example 2 | 5 mg. |
| Corn starch | 244 mg. |
| Magnesium stearate | 1 mg. |

The following examples show representative compounds encompassed by this invention and their synthesis. However, it should be understood that they are for purposes of illustration only.

EXAMPLE 1

Ethyl(±)-erythro-(E)-3,5-dihydroxy-7-[1'-(4''-fluorophenyl)-4'-(1'''-methylethyl)-2'-phenyl-1H-imidazol-5'-yl]hept-6-enoate

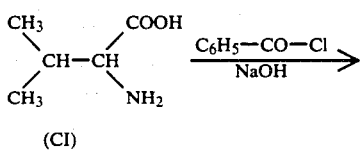

(CI)

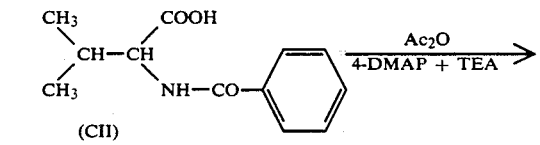

(CII)

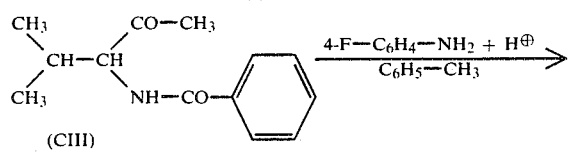
(CIII)
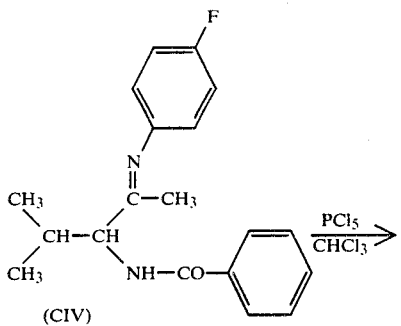
(CIV)
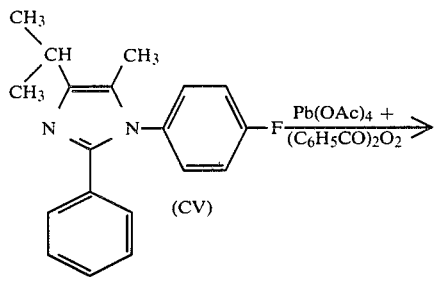
(CV)
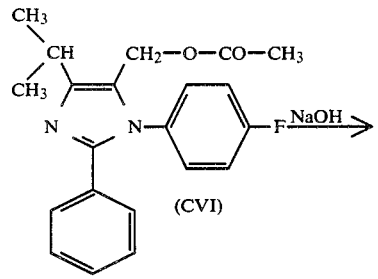
(CVI)
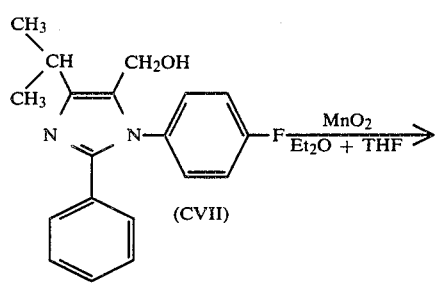
(CVII)
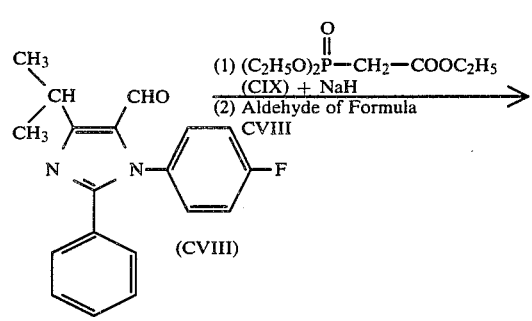
(CVIII)
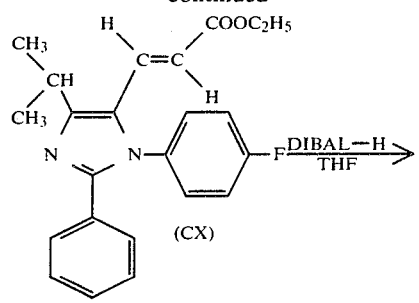
(CX)
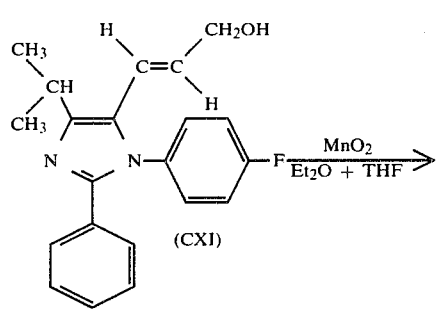
(CXI)
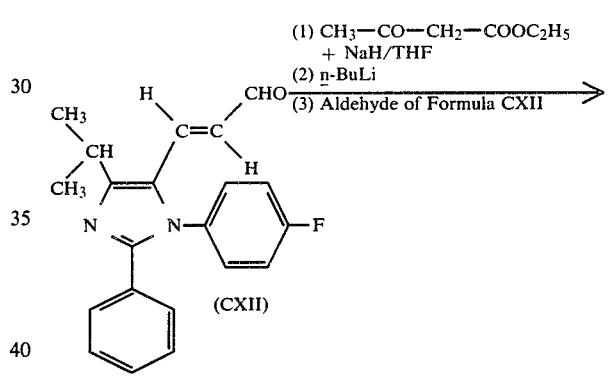
(CXII)
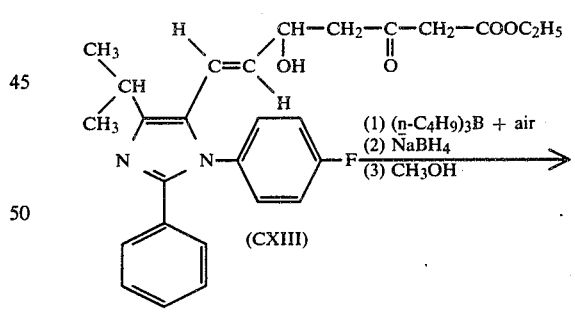
(CXIII)
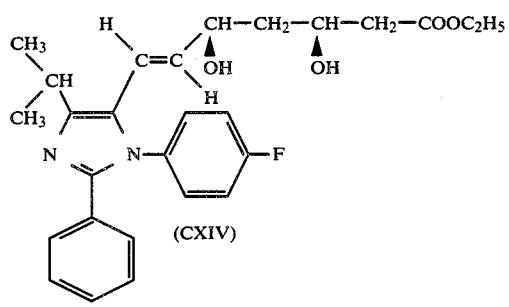
(CXIV)

Step 1 (Reaction AA)

N-Benzoyl-DL-valine (Compound CII)

119 ml. (1.025 moles) of benzoyl chloride and 760 ml. of 2N. sodium hydroxide solution (1.52 moles) are simultaneously added to a mixture of 100 g. (0.854 mole) of DL-valine, 200 ml. of dioxane and 350 ml. of 2N. sodium hydroxide solution (0.7 mole) stirred at 0°-5° C., the additions being at rates such that the pH of the reaction mixture is always basic and the temperature does not exceed 5° C., the reaction being exothermic. the reaction mixture is allowed to warm to 20°-25° C., stirred at 20°-25° C. for 2 hours, cooled to 0° C. and acidified with about 40 ml. of concentrated sulfuric acid. The precipitate is collected by filtration, washed with water, air dried for 16 hours and dissolved in ethyl acetate. The ethyl acetate solution is decanted from some residual water, and petroleum ether is added to obtain a precipitate. The precipitate is subjected to high vacuum for 8 hours to remove some residual dioxane and obtain the product (165.81 g. (88%)), m.p. 125°-128° C. Lit.: 132° C.

Step 2 (Reaction AB)

($\pm$)-N-[1-(1'-methylethyl)-2-oxopropyl]benzamide (Compound CIII)

7.4 g. (60.6 mmoles, a catalytic amount) of 4-dimethylaminopyridine is added in two portions to a mixture of 134 g. (0.606 mole) of Compound CII, 172 ml. (185.6 g., 1.818 moles) of acetic anhydride and 169 ml. (122.6 g., 1.212 moles) of triethylamine stirred at 20°-25° C. under nitrogen, and the reaction mixture is stirred at 20°-25° C. under nitrogen for 16 hours, cooled to 0°-5° C. and quenched with 350 ml. of methanol. The mixture is poured into 2 l. of ice-water, and the precipitated solid is collected by filtration, washed with about 4 l. of water and allowed to air dry for 16 hours. The resulting brown powder is recrystallized from diethyl ether, and the obtained tan needles are recrystallized from diethyl ether to obtain the product (58.83 g.), m.p. 89.5°-91.5° C. A second crop may be obtained from the combined mother liquors.

Step 3 (Reaction AC)

($\pm$)-N-[2-(4'-Fluorophenyl)imino-1-(1'-methylethyl)-propyl]benzamide (Compound CIV)

A mixture of 72.91 g. (332.5 mmoles) of Compound CIII, 35 ml. (40.63 g., 365.7 mmoles) of 4-fluoroaniline, a catalytic amount (50 mg.) of p-toluenesulfonic acid monohydrate and 500 ml. of dry toluene (dried over alumina) is refluxed in a Dean-Stark apparatus for 16 hours under nitrogen, the reaction mixture is allowed to cool, and the toluene is evaporated at reduced pressure to obtain the crude product as a black oil.

Step 4 (Reaction AD)

1-(4'-Fluorophenyl)-5-methyl-4-(1'-methylethyl)-2-phenyl-1H-imidazole (Compound CV)

A solution of crude Compound CIV from Step 3 (332.5 mmoles assuming 100% yield) in 250 ml. of chloroform is added dropwise to a suspension of 138.5 g. (665 mmoles) of phosphorus pentachloride in 500 ml. of chloroform stirred at $-20°$-$15°$ C. under nitrogen. The reaction mixture is allowed to warm to 20°-25° C. with stirring and stirred at 20°-25° C. for 16 hours, the reaction mixture being maintained under nitrogen throughout. The reaction mixture is quenched with 500 ml. of water and made basic with 10% sodium hydroxide solution. The organic phase is separted, washed twice with saturated sodium chloride solution, dried over anhydrous magnesium sulfate, filtered and concentrated at reduced pressure. The obtained pale green solid is recrystallized from acetone to obtain the product as white needles (54.83 g.), m.p. 145°-148° C. A 10.83 g. second crop may be obtained from the acetone mother liquor.

Step 5 (Reaction AE)

5-Acetoxymethyl-1-(4'-fluorophenyl)-4-(1'-methylethyl)-2-phenyl-1H-imidazole (Compound CVI)

A mixture of 21.75 g. (73.9 mmoles) of Compound CV, 65.5 g. (148 mmoles) of lead tetraacetate, 0.05 g. (0.21 mmole) of benzoyl peroxide and 500 ml. glacial acetic acid is heated at 80° C. for 16 hours under nitrogen, cooled to 0°-5° C. and made basic (pH 8-9) with 10N. sodium hydroxide solution. The resulting suspension is filtered through a pad of Celite, the Celite is washed with water and ethyl acetate successively, and the washings are combined with the initial filtrate. The organic phase is separated, and the aqueous phase is extracted with ethyl acetate. The organic phases are combined, washed twice with saturated sodium chloride solution, dried over anhydrous magnesium sulfate, filtered and evaporated at reduced pressure to obtain the crude product as a dark brown foam (22.94 g.).

Step 6 (Reaction AF)

1-(4'-Fluorophenyl)-4-(1'-methylethyl)-2'-phenyl-1H-imidazole-5-methanol (Compound CVII)

100 ml. of 10% sodium hydroxide solution is added to a solution of 22.94 g. ($\leqq 65.1$ mmoles) of crude Compound CVI from Step 5 in absolute ethanol, and the resulting reaction mixture is stirred at 20°-25° C. under nitrogen for 4 hours. The ethanol is evaporated at reduced pressure, and the resulting yellow paste is partitioned between ethyl acetate and water. The ethyl acetate phase is separated, and the aqueous phase is extracted twice with ethyl acetate. The three ethyl acetate phases are combined, washed twice with saturated sodium chloride solution, dried over anhydrous magnesium sulfate, filtered and concentrated at reduced pressure to a volume of about 200 ml. Petroleum ether is added to precipitate the product as a tan powder (11.54 g.). An analytical sample is recrystallized from ethyl acetate. M.p. 183°-186° C.

Step 7 (Reaction J)

1-(4'-Fluorophenyl)-4-(1'-methylethyl)-2-phenyl-1H-imidazole-5-carboxaldehyde (Compound CVIII)

13.45 g. (43.3 mmoles) of Compound CVII is dissolved in 650 ml. of toluene with heating, 53.8 g. (619 mmoles) of activated manganese dioxide is added, the reaction mixture is refluxed under nitrogen for 16 hours with stirring, cooled to 20°-25° C. and filtered through a pad of Celite, the Celite is washed with ethyl acetate, and the filtrate and ethyl acetate washings are combined and evaporated at reduced pressure to a tan solid. The tan solid is recrystallized from diethyl ether to obtain the product (5.12 g.) A second crop is obtained from the mother liquor by adding hexane. M.p. 159°-161° C.

Step 8 (Reaction K)

Ethyl(E)-3-[1'-(4"-fluorophenyl)-4'-(1"-methylethyl)-2'-phenyl-1H-imidazol-5'-yl]propenoate (Compound CX)

(a) 1.8 g. of 60% sodium hydride/mineral oil (45.0 mmoles) is washed twice with hexane, the sodium hydride is suspended in 50 ml. of dry tetrahydrofuran (distilled from ketyl), the suspension is stirred at 20°–25° C., 1 ml. of triethyl phosphonoacetate (Compound CIX) is added, the reaction mixture is cooled to −20°−−15° C. with stirring, 7.6 ml. of Compound CIX is added dropwise with stirring at −20°−−15° C. (the total amount of Compound CIX being 8.6 ml. (9.6 g., 42.84 mmoles)), and the reaction mixture is stirred at −20°−−15° C. for 1 hour to obtain a solution of the ylid, the reaction mixture being stirred under nitrogen throughout.

(b) A solution of 11.0 g. (35.7 mmoles) of Compound CVIII in 100 ml. of dry tetrahydrofuran (distilled from ketyl) is added dropwise to the ylid solution of Part (a) of this step stirred at −20°−−15° C., the reaction mixture is allowed to warm to 20°–25° C. with stirring, an additional 150 ml. of dry tetrahydrofuran (distilled from ketyl) is added to dissolve the solids, and the reaction mixture is stirred at 20°–25° C. for 16 hours, the reaction mixture being maintained under nitrogen throughout. The reaction mixture is poured into water, diethyl ether, ethyl acetate and chloroform are successively added to dissolve all of the solids, the organic phase is separated, the aqueous phase is extracted with chloroform, and the organic phases are combined, washed twice with saturated sodium chloride solution, dried over anhydrous magnesium sulfate, filtered and evaporated at reduced pressure to obtain the product as a pale yellow powder (13.78 g.). An analytical sample is recrystallized from methylene chloride/n-hexane. M.p. 187°–189° C.

Step 9 (Reaction L)

3-[1'-(4"-Fluorophenyl)-4'-(1"-methylethyl)-2'-phenyl-1H-imidazol-5'-yl]prop-2-en-1-ol (Compound CXI)

95.2 mml. of 1.5M. diisobutylaluminum hydride/toluene (142.8 mmoles) is added dropwise to a solution of 13.78 g. (36.4 mmoles) of Compound CX in 350 ml. of dry tetrahydrofuran (distilled from ketyl) stirred at 0° C. under nitrogen, and the reaction mixture is stirred at 0° C. under nitrogen for 45 minutes and quenched at 0° C. with saturated sodium sulfate solution. Sufficient 10% hydrochloric acid is added to dissolve the gel, and the resulting two phase mixture is extracted twice with diethyl ether. The organic phases are combined, washed twice with saturated sodium chloride solution, dried over anhydrous magnesium sulfate, filtered and evaporated to dryness at reduced pressure to obtain the crude product as a pale yellow solid (11.42 g.). A previous batch melted at 190°–193° C. (dec.)

Step 10 (Reaction M)

(E)-3-[1'-(4"-Fluorophenyl)-4'-(1"-methylethyl)-2'-phenyl-1H-imidazol-5'-yl]prop-2-enal (Compound CXII)

11.4 g. (33.9 mmoles) of Compound CXI is dissolved in 250 ml. of dry tetrahydrofuran (distilled from ketyl), 29.5 g. (339 mmoles) of activated manganese dioxide is added, the reaction mixture is stirred at 20°–25° C. for about 3 hours, an additional 29.5 g. (339 mmoles) of activated manganese dioxide is added, and the reaction mixture is stirred at 20°–25° C. for 16 hours and filtered through a pad of Celite. The Celite is washed with ethyl acetate, the washing is combined with the filtrate, and the combined solution is evaporated to dryness at reduced pressure to obtain a yellow solid (10.03 g.). The yellow solid is crystallized from ethyl acetate/hexane to obtain an orange solid (6.74 g.) which is recrystallized from ethyl acetate to obtain the product as a yellow powder (4.29 g.). The mother liquors from the two crystallizations are combined, evaporated to dryness at reduced pressure and flash chromatographed on 300 g. of 230-400 mesh A.S.T.M. silica gel utilizing 30% diethyl ether/hexane as the eluant. The fractions containing the product are combined and evaporated to dryness at reduced pressure, and the residue is recrystallized from ethyl acetate/hexane to obtain additional product (3.72 g.). A previous batch melted at 163°–164° C.

Step 11 (Reaction O)

Ethyl($\pm$)-(E)-7-[1'-(4"-fluorophenyl)-4'-)1"-methylethyl)-2'-phenyl-1H-imidazol-5'-yl]-5-hydroxy-3-oxohept-6-enoate (Compound CXIII)

1.54 g. of 60% sodium hydride/mineral oil (38.5 mmoles) is washed twice with hexane, the remaining powdered sodium hydride is suspended in 100 ml. of dry tetrahydrofuran, the suspension is cooled to −20°−−15° C., 4.55 g. (35.0 mmoles) of ethyl acetoacetate is added dropwise with stirring at −20°−−15° C., the reaction mixture is stirred at −20°−−15° C. for 30 minutes, 23.0 ml. of 1.6M. n-butyllithium/hexane (36.75 mmoles) is added dropwise with stirring at −20°−−15° C., the reaction mixture is stirred at −20°−−15° C. for 10 minutes, a solution of 5.857 g. (17.5 mmoles) of Compound CXII in 100 ml. of dry tetrahydrofuran is added dropwise with stirring at −20°−−15° C., and the reaction mixture is stirred at −20°−−15° C. for 30 minutes, the reaction mixture being maintained under dry argon throughout. The reaction mixture is quenched at −20°−−15° C. with saturated ammonium chloride solution and warmed to 20°–25° C., the tetrahydrofuran is evaporated at reduced pressure, and the residue is partitioned between water and diethyl ether. The aqueous phase is reextracted with diethyl ether, and the diethyl ether phases are combined, washed twice with saturated sodium chloride solution, dried over anhydrous magnesium sulfate, filtered and evaporated at reduced pressure to a yellow foam. The foam is flash chromatographed on 350 g. of 230-400 mesh A.S.T.M. silica gel utilizing 70% diethyl ether/hexane as the eluant to obtain the product as a yellow solid (7.91 g.).

The product is a racemate that may be resolved by conventional means to obtain the 5R and 5S enantiomers.

Step 12 (Reaction P)

Ethyl($\pm$)-erythro-(E)-3,5-dihydroxy-7-[1'-(4"-fluorophenyl)-4'-(1"-methylethyl)-2'-phenyl-1H-imidazol-5'-yl]hept-6-enoate (Compound CXIV)

(a) 34 ml. of 1.0M. tri-n-butylborane/tetrahydrofuran (34.0 mmoles) is added rapidly dropwise to a solution of 7.91 g. (17.0 mmoles) of Compound CXIII in 100 ml. of dry tetrahydrofuran (distilled from ketyl) stirred at 20°–25° C. under nitrogen, air is bubbled in for 1 minute, the reaction mixture is stirred at 20°–25° C. under nitrogen for 1 hour and cooled to −78° C., 3.22 g. (85.0 mmoles) of sodium borohydride is added in one portion, the reaction mixture is stirred at −78° C. under nitrogen for 16 hours, an additional 3.22 g. (85.0 mmoles) of sodium borohydride is added in one portion, and the reaction mixture is stirred at −78° C. under nitrogen for 64 hours, warmed to −25° C., stirred at −25° C. under nitrogen for 16 hours, quenched with 10% hydrochloric acid and partitioned between diethyl ether and water. The aqueous phase is neutralized with saturated sodium bicarbonate solution and extracted with diethyl ether. The two diethyl ether phases are combined, washed twice with saturated sodium chloride solution, dried over anhydrous magnesium sulfate, filtered and evaporated at reduced pressure to a yellow wax (11.79 g.). The yellow wax is recrystallized from isopropanol to obtain a white powder (2.61 g.) which is recrystallized from isopropanol to obtain the cyclic boron ester as a white powder (1.83 g.).

(b) 4.0 g. of the cyclic boron ester of Part (a) of this step is dissolved in methanol with warming (35°–40° C.) and the methanol is evaporated at reduced pressure and 35°–40° C., this procedure is repeated two more times, the residue is dissolved in warm methylene chloride, and hexane is added to obtain the product as a white solid (2.93 g.). A second crop may be obtained from the mother liquor. M.p. 149°–151° C.

N.M.R. (CDCl$_3$): 1.26 (t, 3H), 1.36 (d, 6H), 1.61 (m, 2H), 2.45 (d, 2H), 3.13 (m, 1H), 3.23 (d, 1H) 3.30 (d, 1H), 4.16 (q, 2H), 4.19 (bm, 1H), 4.36 (bm, 1H), 5.50 (dd, 1H), 6.19 (dd, 1H), 7.0–7.37 (m, 9H)

The product, the erythro racemate, may be resolved to obtain the 3R,5S and 3S,5R enantiomers, of which the former is preferred. The use of a non-stereoselective reduction would afford a mixture of all four stereoisomers wherein the ratio of the erythro stereoisomers to the threo stereoisomers ranges from 3:2 to 2:3. A mixture of the erythro and threo racemates wherein the ratio of the former to the latter is about 7:3 may be obtained by omitting the isopropanol recrystallizations from Part (a) of this step.

EXAMPLE 2

Sodium(±)-erythro-(E)-3,5-dihydroxy-7-[1′-(4″-fluorophenyl)-4′-(1‴-methylethyl)-2′-phenyl-1H-imidazol-5′-yl]hept-6-enoate (Reaction R)

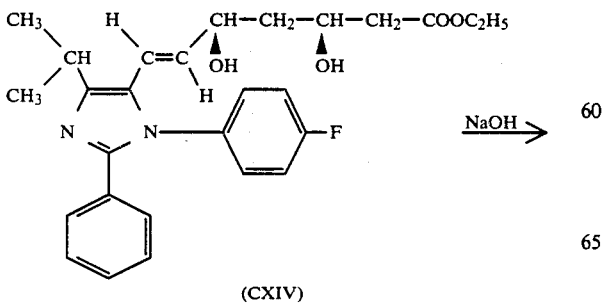

(CXIV)

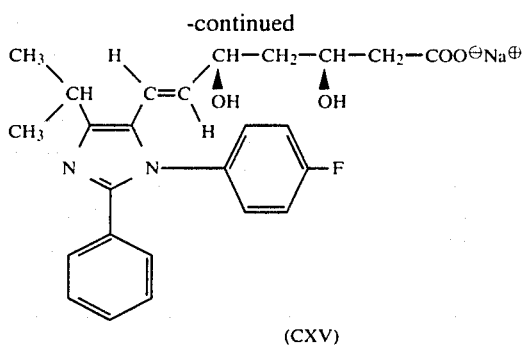

(CXV)

6.2 ml of 1N. sodium hydroxide solution (6.2 mmoles) is added dropwise to a solution of 3.0 g. (6.52 mmoles) of Compound CXIV in 125 ml. of absolute ethanol stirred at 20°–25° C., the reaction mixture is stirred at 20°–25° C. for 2 hours and evaporated at reduced pressure to dryness, the residue is partitioned between water and methylene chloride, sufficient water is added to break the resulting emulsion, the aqueous layer is carefully separated, most of the water is evaporated at reduced pressure, and the resulting slurry is frozen at −78° C. and lyophilized to obtain the product as a pale yellow powder (3.02 g.), m.p. 217°–224° C. (dec.) (softens and loses water at 100°–116° C.)

N.M.R. (CDCl$_3$+CD$_3$SOCD$_3$): 1.32 (d, 6H), 1.53 (m, 2H), 2.30 (m, 2H), 3.13 (m, 1H), 4.08 (bm, 1H, 4.24 (bm, 1H), 5.50 (dd, 1H), 6.18 (dd, 1H), 7.0–7.3 (m, 9H)

The product, the erythro racemate, may be resolved to obtain the 3R,5S and 3S,5R enantiomers, of which the former is preferred. The use of a starting material synthesized by using a non-stereoselective reduction in Step 12 of Example 1 would afford a mixture of all four stereoisomers wherein the ratio of the erythro stereoisomers to the threo stereoisomers ranges from 3:2 to 2:3.

EXAMPLE 3

Ethyl(±)-erythro-(E)-3,5-dihydroxy-7-[4′-(4″-fluorophenyl)-1′-(1‴-methylethyl)-2′-phenyl-1H-imidazol-5′-yl]hept-6-enoate

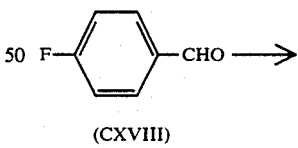

(CXVIII)

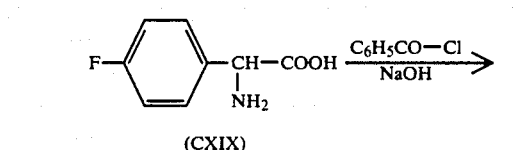

(CXIX)

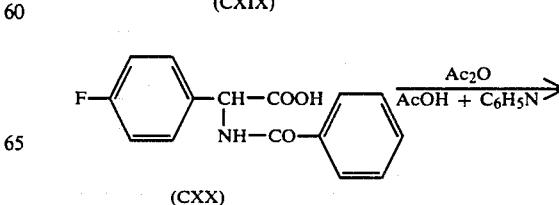

(CXX)

-continued
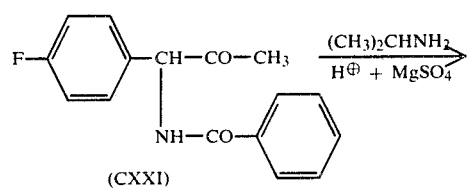
(CXXI)
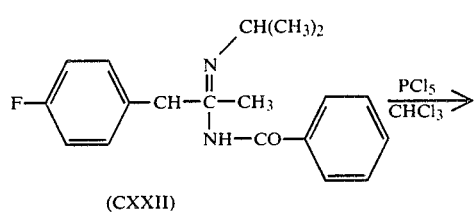
(CXXII)
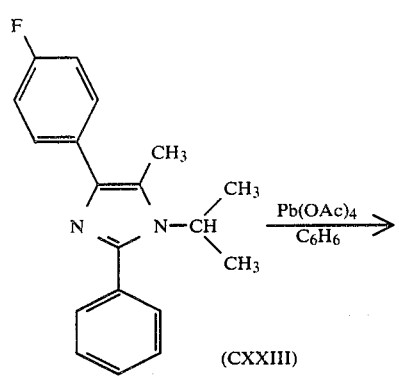
(CXXIII)
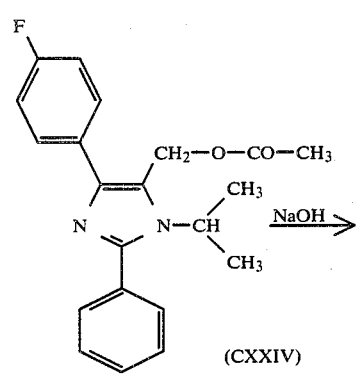
(CXXIV)
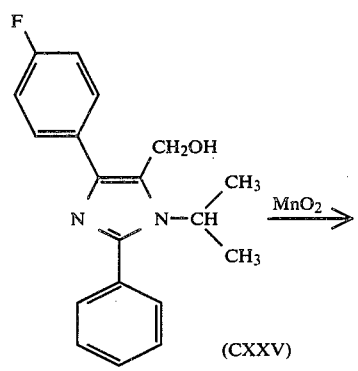
(CXXV)
-continued
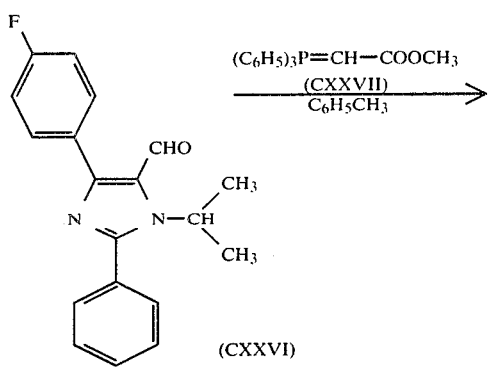
(CXXVI)
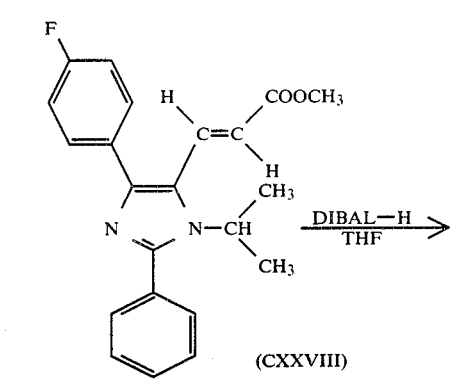
(CXXVIII)
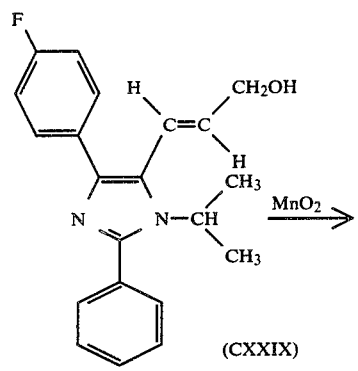
(CXXIX)
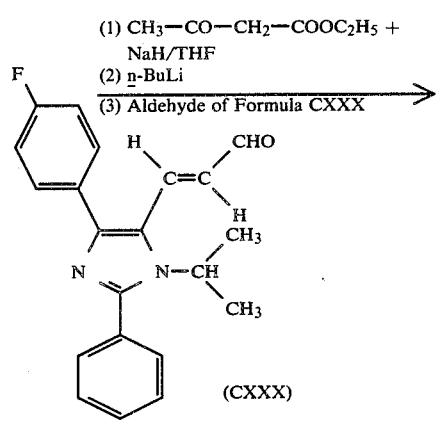
(CXXX)

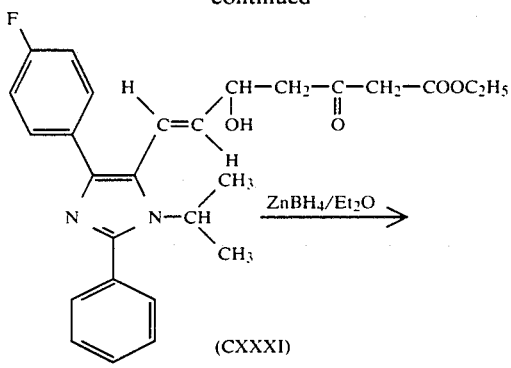

(CXXXI)

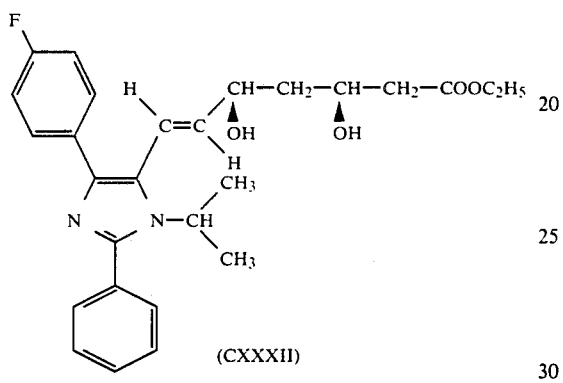

(CXXXII)

Step 1 (Reaction BA)

DL-4-Fluorophenylglycine (Compound CXIX)

800 ml. of saturated ammonium hydroxide solution is slowly added to 67.6 g. (1.59 mmoles) of lithium chloride, 268.8 g. (4.79 moles) of potassium hydroxide is slowly added portionwise (the addition being exothermic), and a solution of 18.4 g. (0.81 mole) of benzyltriethylammonium chloride in 400 ml. of methylene chloride is added, the reaction mixture being stirred at 20°–25° C. under nitrogen throughout. The reaction mixture is cooled to 0° C., ammonia is bubbled in for 30 minutes with vigorous stirring, and, over a period of 1 hour, a solution of 99.2 g. (0.80 mole) of 4-fluorobenzaldehyde in a mixture of 400 ml. of methylene chloride and 102 ml. of chloroform is added dropwise while simultaneously bubbling in ammonia, the reaction mixture being stirred at 0° C. throughout. Ammonia is bubbled in for 5 hours with stirring at 0° C., and the reaction mixture is allowed to warm to 20°–25° C. and stirred at 20°–25° C. for 16 hours. The aqueous phase is separated, washed three times with 150 ml. portions of methylene chloride, concentrated to one half of its volume at reduced pressure and filtered. The filtrate is acidified to pH 6.5 with concentrated hydrochloric acid, and the resulting fine precipitate is collected by filtration, washed with 1.5 l. of water, washed with 500 ml. of ethanol, washed with 200 ml. of diethyl ether and dried to obtain the product as a fine white solid (40 g.). A previous batch melted at about 280° C. (softened at about 260° C.).

Step 2 (Reaction BB)

N-Benzoyl-DL-4-fluorophenylglycine (Compound CXX)

A solution of 23.2 ml. (28.1 g., 200 mmoles) of benzoyl chloride in 70 ml. of dioxane and 500 ml. of 2N. sodium hydroxide solution (1 mole) are simultaneously added dropwise over a period of about 45 minutes to a solution of 25.35 g. (150 mmoles) of Compound CXIX in a mixture of 300 ml. of dioxane and 600 ml. of 2N. sodium hydroxide solution (1.2 moles) stirred at 0° C. under nitrogen, the additions being at rates such that the pH of the reaction mixture is always basic and the temperature is 0° C., the reaction being exothermic. The reaction mixture is stirred at 0° C. under nitrogen for 1 hour and warmed to 20°–25° C., the tetrahydrofuran is evaporated at reduced pressure, and the mixture is acidified to pH 1 with concentrated hydrochloric acid and cooled to 0° C. The obtained white solid is collected by filtration, washed with 2 l. of distilled water, air dried and vacuum dried to obtain the product as a white powder (31.4 g.). An analytical sample is recrystallized from ethanol/water. M.p. 169°–171° C.

Step 3 (Reaction BC)

(±)-N-[1-(4'-Fluorophenyl)-2-oxopropyl]benzamide (Compound CXXI)

50 ml. (618 mmoles) of pyridine and 50 ml. (530 mmoles) of acetic anhydride are added to 30 g. (110 moles) of Compound CXX, the mixture is stirred at 20°–25° C., 100 mg. (0.82 mmole) of 4-dimethylaminopyridine is added, the reaction mixture is stirred at 20°–25° C. for 45 minutes, 150 ml. (2.62 mmoles) of glacial acetic acid is added, and the reaction mixture is stirred at 130° C. for 3 hours and cooled to 20°–25° C., the reaction mixture being maintained under nitrogen throughout. The reaction mixture is cooled to 0°–5° C., 100 ml. of methanol is added, and the reaction mixture is stirred at 0°–5° C. for 30 minutes and poured into 1.5 l. of ice water. The mixture is allowed to stand for 16 hours, and the precipitate is collected by filtration, washed with 2 l. of distilled water and air dried to obtain a yellow powder which is recrystallized from methanol to obtain the yellow crystalline product (8.6 g.), m.p. 134°–136° C. A second crop is obtained from the mother liquor by adding water and cooling (2.5 g.).

Step 4 (Reaction BD)

(±)-N-[1-(4'-Fluorophenyl)-2-(1'-methylethyl)imino-propyl]benzamide (Compound CXXII)

100 mg. (0.53 mmole) of p-toluenesulfonic acid monohydrate is added to a solution of 5.42 g. (20.0 mmoles) of Compound CXXI and 8.2 ml. (5.69 g., 96.3 mmoles) of isopropylamine in 100 ml. of benzene and 25 ml. of methylene chloride, 25 g. (208 mmoles) of anhydrous magnesium sulfate is added, the reaction mixture is stirred at 20°–25° C. under nitrogen for 48 hours, an additional 16.4 ml. (11.38 g., 192.6 mmoles) of isopropylamine and 50 g. (415 mmoles) of anhydrous magnesium sulfate are added, the reaction mixture is stirred at 20°–25° C. under nitrogen for 4 hours, an additional 10 g. (42 mmoles) of anhydrous magnesium sulfate is added, and the reaction mixture is stirred at 20°–25° C. under nitrogen for 64 hours and filtered. The solid is washed with methylene chloride, the washing is combined with the filtrate, and the combined filtrate and washing is evaporated at reduced pressure to obtain the crude product as a yellow oil (about 7.5 g.).

Step 5 (Reaction BE)

4-(4'-Fluorophenyl)-5-methyl-1-(1'-methylethyl)-2-phenyl-1H-imidazole (Compound CXXIII)

A solution of about 7.5 g. ($\leq$20 mmoles) of crude Compound CXXII from Step 4 in 50 ml. of chloroform is added over a 30 minute period to 8.12 g. (39 mmoles) of phosphorus pentachloride in 100 ml. of chloroform stirred at $-30°$ C., and the reaction mixture is allowed to warm to 20°–25° C., stirred at 20°–25° C. for 16 hours and cooled to 0° C., the reaction mixture being stirred under nitrogen throughout. 10 ml. of water is added, the mixture is stirred for 5 minutes, and 200 ml. of 2N. sodium hydroxide solution is added. The organic phase is separated, and the aqueous phase is extracted with chloroform. The chloroform extract and the organic phase are combined, washed twice with saturated sodium chloride solution, dried over anhydrous magnesium sulfate, filtered and evaporated at reduced pressure to a tan solid. The tan solid is recrystallized from benzene to obtain the product as a white solid (2.33 g.). A second crop is obtained from the mother liquor (200 mg.). An analytical sample is recrystallized from aqueous ethanol. M.p. 161°–162° C.

Step 6 (Reaction BF)

5-Acetoxymethyl-4-(4'-fluorophenyl)-1-(1'-methylethyl)-2-phenyl-1H-imidazole (Compound CXXIV)

3.5 g. (7.9 mmoles) of lead tetraacetate is added to a solution of 2.30 g. (7.81 mmoles) of Compound CXXIII in 300 ml. of dry benzene, and the reaction mixture is refluxed under nitrogen for 3 hours, an additional 0.35 g. (0.79 mmole) of lead tetraacetate is added, the reaction mixture is refluxed under nitrogen for 30 minutes, an additional 0.70 g. (1.58 mmoles) of lead tetraacetate is added, and the reaction mixture is refluxed under nitrogen for 1 hour, cooled, filtered and evaporated at reduced pressure to obtain the crude product as a tan gum (3.59 g.).

Step 7 (Reaction BG)

4-(4'-Fluorophenyl)-1-(1'-methylethyl)-2-phenyl-1H-imidazole-5-methanol (Compound CXXV)

100 ml. of 2N. sodium hydroxide solution (200 mmoles) is added to a solution of 3.59 g. ($\leq$7.81 mmoles) of crude Compound CXXIV (from Step 6) in 100 ml. of ethanol, the reaction mixture is stirred at 20°–25° C. under nitrogen for 16 hours, the ethanol is evaporated at reduced pressure, 200 ml. of water is added, the mixture is stirred for 2 minutes, and the insoluble solid is collected by filtration, washed with 200 ml. of water (until the washings are pH 7) and dried to obtain the crude product as a yellow solid (1.88 g.). An analytical sample is recrystallized from aqueous ethanol. M.p. 190°–193° C.

Step 8 (Reaction J)

4-(4'-Fluorophenyl)-1-(1'-methylethyl)-2-phenyl-1H-imidazole-5-carboxaldehyde (Compound CXXVI)

10 g. (115 mmoles) of activated manganese dioxide is added to a solution of 1.55 g. (5.0 mmoles) of Compound CXXV in 50 ml. of tetrahydrofuran, and the reaction mixture is stirred at 20°–25° C. under nitrogen for 16 hours and filtered. The solid is washed with 100 ml. of tetrahydrofuran, and the washing and filtrate are combined and evaporated at reduced pressure to obtain a yellow oil which is vacuum dried to obtain a yellow solid. The yellow solid is recrystallized from diethyl ether/hexane to obtain the yellow crystalline product (1.2 g.), m.p. 130°–134° C.

Step 9 (Reaction K)

Methyl (E)-3-[4'-(4''-fluorophenyl)-1'-(1''-methylethyl)-2'-phenyl-1H-imidazol-5'-yl]propenoate (Compound CXXVIII)

2.004 g. (6.0 mmoles) of (carbomethoxymethylene)triphenylphosphorane (Compound CXXVII) is added to a solution of 1.23 g. (4.0 mmoles) of Compound CXXVI in 25 ml. of dry toluene, the reaction mixture is refluxed under nitrogen for 5 hours and stirred at 20°–25° C. under nitrogen for 16 hours, an additional 200 mg. (0.6 mmole) of Compound CXXVII is added, and the reaction mixture is refluxed under nitrogen for 1 hour, allowed to cool, evaporated at reduced pressure to about one half of its volume and flash chromatographed on 150 g. of 230–400 mesh A.S.T.M. silica gel utilizing 1:1 diethyl ether/hexane as the eluant to obtain the product as a pale yellow solid (1.22 g.). An analytical sample is recrystallized from diethyl ether. M.p. 129°–131° C.

Step 10 (Reaction L)

(E)-3-[4'-(4''-Fluorophenyl)-1'-(1''-methylethyl)-2'-phenyl-1H-imidazol-5'-yl]prop-2-en-1-ol (Compound CXXIX)

10 ml. of 1.5M. diisobutylaluminum hydride/toluene (15 mmoles) is added dropwise over a period of 5 minutes to a solution of 1.092 g. (3.0 mmoles) of Compound CXXVIII in 50 ml. of dry tetrahydrofuran stirred at 0° C. under nitrogen, and the reaction mixture is stirred at 0° C. under nitrogen for 2 hours and quenched with 0.5 ml. of saturated ammonium chloride solution. 5 ml. of water is added to dissolve the precipitate, 100 ml. of saturated sodium chloride solution and 50 ml. of 10% sodium hydroxide solution are added, the organic phase is separated, the aqueous phase is extracted three times with 50 ml. portions of diethyl ether, and the organic phase and the three diethyl ether extracts are combined, washed with 100 ml. of saturated sodium chloride solution, dried over anhydrous magnesium sulfate, filtered and evaporated at reduced pressure to obtain the product as a colorless oil which solidifies upon standing (910 mg.).

Step 11 (Reaction M)

(E)-3-[4'-(4''-Fluorophenyl)-1'-(1''-methylethyl)-2'-phenyl-1H-imidazol-5'-yl]prop-2-enal (Compound CXXX)

8 g. (92 mmoles) of activated manganese dioxide is added to a solution of 900 mg. (2.68 mmoles) of Compound CXXIX in 100 ml. of 1:1 diethyl ether/tetrahydrofuran, and the reaction mixture is stirred at 20°–25° C. under nitrogen for 1 hour and filtered through a pad of Celite. The solid is washed with 100 ml. of diethyl ether and washed with 100 ml. of tetrahydrofuran, the two washing are combined with the filtrate, and the combined washings and filtrate are evaporated at reduced pressure to obtain a yellow oil (740 mg.) which solidifies upon standing. The solid is recrystallized from diethyl ether to obtain the product as yellow needles (405 mg.). The residue from the mother liquor is recrystallized from aqueous ethanol to obtain a second crop (74 mg.) and a third crop (55 mg.). Additional product may be obtained by chromatographing the residue from the mother liquor from the third crop on 10 g. of silica gel utilizing 2:1 diethyl ether/hexane as the eluant (44 mg.).

Step 12 (Reaction O)

Ethyl(±)-(E)-7-[4'-(4''-fluorophenyl)-1'-(1''-methylethyl)-2'-phenyl-1H-imidazol-5'-yl]-5-hydroxy-3-oxohept-6-enoate (Compound CXXXI)

21.12 mg. of 50% sodium hydride/mineral oil (0.44 mmole) is washed with 3 ml. of hexane, the liquid is decanted, 5 ml. of dry tetrahydrofuran is added, the suspension is cooled to −15° C., 51 μl. (52 mg., 0.40 mmole) of ethyl acetoacetate is added via syringe, the reaction mixture is stirred at −15° C. for 1.5 hours, allowed to warm to 0° C., stirred at 0° C. for 1 hour and cooled to −15° C., 0.31 ml. of 1.6M. n-butyllithium/hexane (0.50 mmole) is added with stirring at −15° C., the reaction mixture is stirred at −15° C. for 10 minutes, a solution of 66.8 mg. (0.20 mmole) of Compound CXXX in 3 ml. of dry tetrahydrofuran is added dropwise with stirring at −15° C., and the reaction mixture is stirred at −15° C. for 15 minutes, the reaction mixture being maintained under nitrogen throughout. The reaction mixture is quenched at −15° C. with 5 drops of saturated ammonium chloride solution, the tetrahydrofuran is evaporated at reduced pressure, diethyl ether and saturated sodium chloride solution are added, and the organic layer is separated, washed twice with 25 ml. portions of saturated sodium chloride solution, dried over anhydrous magnesium sulfate, filtered and evaporated at reduced pressure to obtain a gum (92 mg.). The gum is chromatographed on 5 g. of 230–400 mesh A.S.T.M. silican gel utilizing 9:1 diethyl ether/hexane as the eluant to obtain the product as a pale yellow gum (39.1 mg.).

The product is a racemate that may be resolved by conventional means to obtain the 5R and 5S enantiomers.

Step 13 (Reaction P)

Ethyl (±)-erythro-(E)-3,5-dihydroxy-7-[4'-(4''-fluorophenyl)-1'-(1''-methylethyl)-2'-phenyl-1H-imidazol-5'-yl]hept-6-enoate (Compound CXXXII)

A solution of 39 mg. (0.084 mmole) of Compound CXXXI in 1 ml. of anhydrous diethyl ether is added dropwise via syringe over a period of 5 minutes to 2.4 ml. of 0.15M. zinc borohydride/diethyl ether (0.36 mmole) stirred at −65° C. under nitrogen, and the reaction mixture is stirred at −65° C. under nitrogen for 2 hours and quenched at −65° C. with 0.5 ml. of methanol. The mixture is stirred for 3 minutes, 1 ml. of water is added, the mixture is allowed to warm to 20°–25° C., 10 ml. of very dilute acetic acid is added, 10 ml. of diethyl ether is added, and the organic phase is separated, washed twice with 20 ml. portions of saturated sodium chloride solution, dried over anhydrous magnesium sulfate, filtered and evaporated at reduced presure to a yellow oil. The yellow oil is chromatographed on 10 g. of 230–400 mesh A.S.T.M. silica gel utilizing 30% ethyl acetate/chloroform as the eluant. The fractions containing the product (as indicated by thin layer chromatography) are combined and evaporated at reduced pressure, and the obtained pale yellow oil is vacuum dried to obtain the product as a solid foam (31 mg.).

N.M.R. (CDCl$_3$): 1.28 (t, 3H), 1.48 (d, 6H), 1.56 (m, 2H) 2.46 (d, 2H), 4.18 (q, 2H), 4.21 (bm, 1H), 4.47 (bm, 1H), 4.59 (m, 1H), 5.78 (dd, 1H), 6.7 (d, 1H), 6.98 (t, 2H), 7.4–7.7 (m, 7H)

The product is a mixture of the erythro and threo racemates wherein the ratio of the former to the latter is about 17:3, which mixture may be separated by conventional means. The principal product, the erythro racemate, may be resolved into two optically pure enantiomers, the 3R,5S and 3S,5S enantiomers, of which the former is preferred. The minor product, the threo racemate, may be resolved to obtain the 3R,5R and 3S,5S enantiomers. The use of a non-stereoselective reduction would afford a mixture of all four stereoisomers wherein the ratio of the erythro stereoisomers to the threo stereoisomers ranges from 3:2 to 2:3.

EXAMPLE 4

Sodium (±)-erythro-(E)-3,5-dihydroxy-7-[4'-(4''-fluorophenyl)-1'-(1''-methylethyl)-2'-phenyl-1H-imidazol-5'-yl]hept-6-enoate (Reaction R)

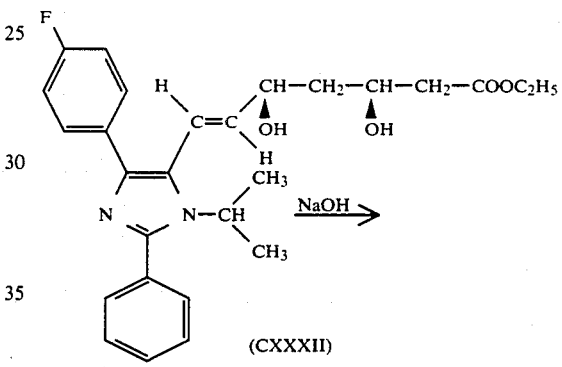

(CXXXII)

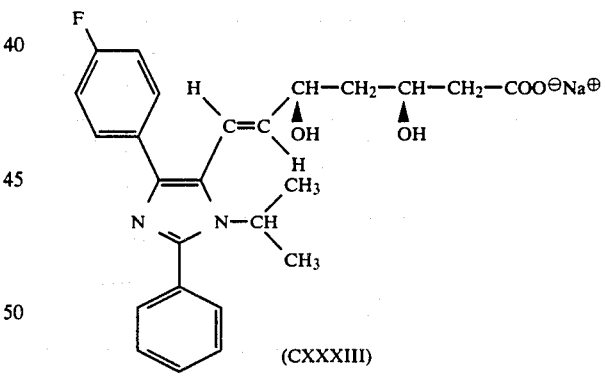

(CXXXIII)

0.04 ml. of 0.5N. sodium hydroxide solution (0.02 mmole) is added to a solution of 10 mg. (0.0214 mmole) of Compound CXXII in 1 ml. of ethanol and 10 drops of water, the reaction mixture is stirred at 20°–25° C. under nitrogen for 1 hour, the ethanol is evaporated at reduced pressure, 0.5 ml. of water is added, and the mixture is extracted three times with 5 ml. portions of diethyl ether. The aqueous phase is lyophilized to obtain the product as a pale yellow solid (9.8 mg.).

N.M.R. (CDCl$_3$+CD$_3$OD): 1.45 (d, 6H), 1.55 (m, 2H), 2.35 (m, 2H), 4.14 (bm, 1H), 4.40 (bm, 1H), 4.57 (m, 1H), 5.75 (dd, 1H), 6.67 (d, 1H), 6.98 (t, 2H), 7.4–7.7 (m, 7H)

The product is a mixture of the erythro and threo racemates wherein the ratio of the former to the latter is about 17:3, which mixture may be separated by conventional means. The principal product, the erythro racemate, may be resolved into two optically pure enantiomers, the 3R,5S and 3S,5R enantiomers, of which the former is preferred. The minor product, the threo racemate, may be resolved to obtain the 3R,5R and 3S,5S enantiomers. The use of a starting material synthesized by using a non-stereoselective reduction in Step 13 of Example 3 would afford a mixture of all four stereoisomers wherein the ratio of the erythro stereoisomers to the threo stereoisomers ranges from 3:2 to 2:3.

EXAMPLE 5

Ethyl (±)-(E)-3,5-dihydroxy-7-[1'-(4''-fluorophenyl)-4'-(1''-methylethyl)-2'-phenyl-1H-imidazol-5'-yl]hept-6-enoate.hydrochloride (Reaction X)

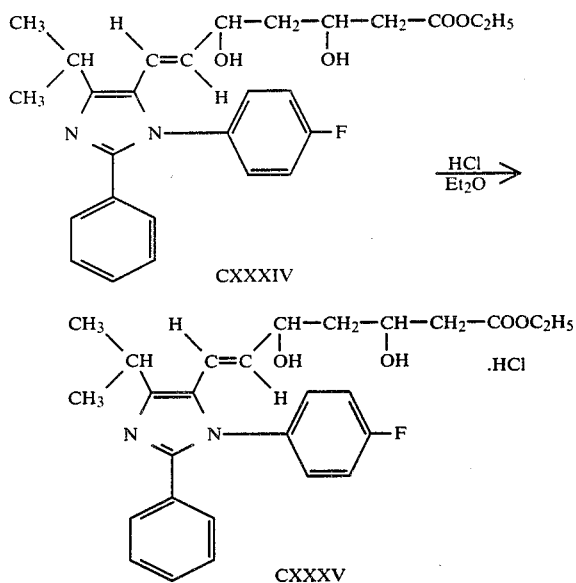

Hydrogen chloride is bubbled for 10 minutes through a solution of 18.5 mg. of Compound CXXXIV wherein the ratio of the erythro racemate to the threo racemate is about 7:3 in diethyl ether stirred at 20°-25° C., the diethyl ether is evaporated at reduced pressure, the resulting gum is dissolved in methylene chloride and the methylene chloride is evaporated at reduced pressure to obtain the product as a yellow foam. M.p. 85°-95° C.

The product is a mixture of the erythro and threo racemates wherein the ratio of the former to the latter is about 7:3.

EXAMPLES 6 and 7

The following compounds of Group IAa may be synthesized by the processes set forth above:

Ex. 7 ($CDCl_3 + CD_3OD$): 1.35 (d (J=7 Hz.), 6H), 1.35-1.70 (m, 2H), 2.26 (s, 6H), 2.10-2.40 (m, 2H), 3.15 (sp (J=7 Hz.), 1H), 3.50 (water), 4.08 (m, 1H), 4.28 (m, 1H), 5.50 (dd ($J_1$=16 Hz., $J_2$=6 Hz.), 1H), 6.18 (d (J=16 Hz.), 1H), 6.77 (s, 2H), 7.00 (s, 1H), 7.15-7.35 (m, 5H)

The compound of Examples 6 and 7 are erythro racemates. The may contain a very small amount (less than 2%) of the corresponding threo racemates which may be separated therefrom. Each erythro racemate may be resolved to obtain the 3R,5S and 3S,5R enantiomers, of which the former is preferred.

Each of the compounds of the examples wherein Z is a group of Formula a wherein $R_{11}$ is a cation may be converted into the corresponding compounds wherein $R_{11}$ is hydrogen or a different cation M, particularly the latter, especially M', by the processes set forth in Reaction Scheme IV. Each of the compounds of the examples except those wherein Z is a group of Formula a wherein $R_{11}$ is a cation and the one already in pharmaceutically acceptable acid addition salt form may be converted into pharmaceutically acceptable acid addition salt form as also set forth in Reaction Scheme IV.

Each of Examples 1-7 (including each of the possible optical isomers of each example) may be administered to an animal, e.g., a larger primate, to inhibit cholesterol biosynthesis and thereby lower the blood cholesterol level for, for example, the treatment of atherosclerosis and hyperlipoproteinemia. The dosages are those set forth supra.

Throughout the examples, the term "reduced pressure" denotes aspirator pressure. Where no solvent is specified in connection with a solution, the solvent is water, and all solvent mixtures are by volume. When a reaction is carried out under nitrogen or argon, dry nitrogen or argon, as the case may be, is used to maintain anhydrous conditions (except where the reaction medium contains water).

All nuclear magnetic resonance spectra were taken at ambient temperature on a 200 MHz. spectrometer. All chemical shifts are given in p.p.m. (δ) relative to tetramethylsilane, and where a single δ value is given for anything other than a sharp singlet, it is its center point. In the N.M.R. data:
bm=broad multiplet
d=doublet
dd=doublet of a doublet
m=multiplet
q=quartet
s=singlet
sp=septet
t=triplet

What is claimed is:
1. A compound of the formula

|        | $R_1$     | $R_2$ | $R_3$ | $R_4$ | $R_5$    | $R_6$    | $R_7$ | X          | $R_{11}$ | Isomers | M.p. |
|--------|-----------|-------|-------|-------|----------|----------|-------|------------|----------|---------|------|
| Ex. 6  | i-$C_3H_7$ | H     | H     | H     | 3-$CH_3$ | 5-$CH_3$ | H     | (E)—CH=CH— | $C_2H_5$ | E       | 73°-75° C. |
| Ex. 7  | i-$C_3H_7$ | H     | H     | H     | 3-$CH_3$ | 5-$CH_3$ | H     | (E)—CH=CH— | $Na^\oplus$ | E    | Fluffy solid (contains some water) |

E = erythro racemate

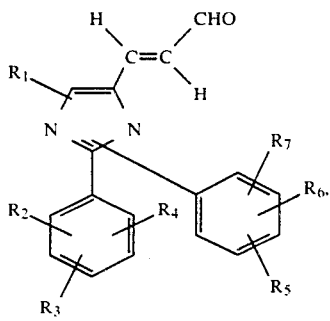

wherein
R₁ is $C_{1-6}$alkyl not containing an asymmetric carbon atom, each of R₂ and R₅ is independently hydrogen, $C_{1-3}$alkyl, n-butyl, i-butyl, t-butyl, $C_{1-3}$alkoxy, n-butoxy, i-butoxy, trifluoromethyl, fluoro, chloro, phenyl, phenoxy or benzyloxy, each of R₃ and R₆ is independently hydrogen, $C_{1-3}$alkyl, $C_{1-3}$alkoxy, trifluoromethyl, fluoro, chloro, phenoxy or benzyloxy, and each of R₄ and R₇ is independently hydrogen, $C_{1-2}$alkyl, $C_{1-2}$alkoxy, fluoro or chloro, with the provisos that not more than one of R₂ and R₃ is trifluoromethyl, not more than one of R₂ and R₃ is phenoxy, not more than one of R₂ and R₃ is benzyloxy, not more than one of R₅ and R₆ is trifluoromethyl, not more than one of R₅ and R₆ is phenoxy, and not more than one of R₅ and R₆ is benzyloxy.

2. A compound according to claim 1 having the formula

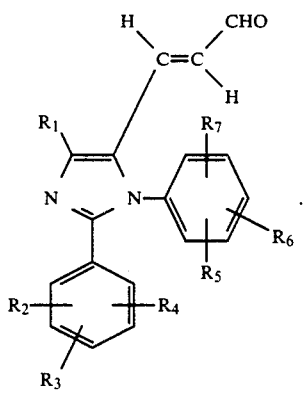

3. A compound according to claim 2 wherein
R₁ is $C_{1-3}$alkyl, n-butyl or i-butyl,
R₂ is hydrogen, $C_{1-3}$alkyl, $C_{1-2}$alkoxy, trifluoromethyl, fluoro or chloro,
R₃ is hydrogen, $C_{1-2}$alkyl, fluoro or chloro,
R₄ is hydrogen or methyl,
R₅ is hydrogen, $C_{1-3}$alkyl, $C_{1-2}$alkoxy, trifluoromethyl, fluoro or chloro,
R₆ is hydrogen, $C_{1-2}$alkyl, fluoro or chloro, and
R₇ is hydrogen or methyl.

4. A compound according to claim 3 wherein
R₂ is hydrogen, methyl or fluoro,
R₃ is hydrogen or methyl,
R₄ is hydrogen,
R₅ is hydrogen, methyl or fluoro,
R₆ is hydrogen or methyl, and
R₇ is hydrogen.

5. A compound according to claim 4 wherein R₁ is $C_{1-3}$alkyl.

6. The compound according to claim 5 having the formula

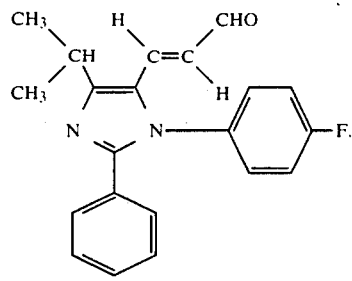

7. A compound according to claim 1 having the formula

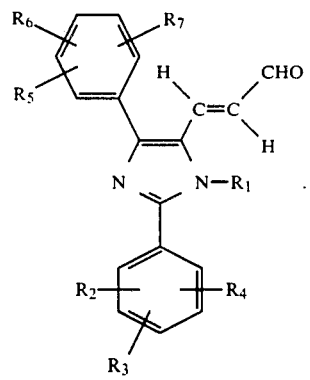

8. A compound according to claim 7 wherein
R₁ is $C_{1-3}$alkyl, n-butyl or i-butyl,
R₂ is hydrogen, $C_{1-3}$alkyl, $C_{1-2}$alkoxy, trifluoromethyl, fluoro or chloro,
R₃ is hydrogen, $C_{1-2}$alkyl, fluoro or chloro,
R₄ is hydrogen or methyl,
R₅ is hydrogen, $C_{1-3}$alkyl, $C_{1-2}$alkoxy, trifluoromethyl, fluoro or chloro,
R₆ is hydrogen, $C_{1-2}$alkyl, fluoro or chloro, and
R₇ is hydrogen or methyl.

9. A compound according to claim 8 wherein
R₂ is hydrogen, methyl or fluoro,
R₃ is hydrogen or methyl,
R₄ is hydrogen,
R₅ is hydrogen, methyl or fluoro,
R₆ is hydrogen or methyl, and
R₇ is hydrogen.

10. A compound according to claim 9 wherein R₁ is $C_{1-3}$alkyl.

11. The compound according to claim 10 having the formula

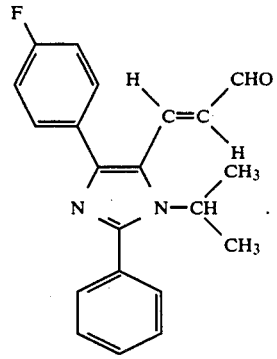

* * * * *